(12) United States Patent
Palmer et al.

(10) Patent No.: US 9,596,548 B2
(45) Date of Patent: Mar. 14, 2017

(54) SOUND PROCESSOR APPARATUSES THAT FACILITATE BATTERY TYPE DETECTION AND COMMUNICATION WITH A PROGRAMMING SYSTEM

(71) Applicant: ADVANCED BIONICS AG, Staefa (CH)

(72) Inventors: Logan P. Palmer, Santa Monica, CA (US); Roger S. Meier, Canyon Country, CA (US); R. Tissa Karunasiri, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 14/761,000

(22) PCT Filed: Jan. 15, 2013

(86) PCT No.: PCT/US2013/021604
§ 371 (c)(1),
(2) Date: Jul. 14, 2015

(87) PCT Pub. No.: WO2014/112982
PCT Pub. Date: Jul. 24, 2014

(65) Prior Publication Data
US 2015/0373463 A1 Dec. 24, 2015

(51) Int. Cl.
*H04R 25/00* (2006.01)
*A61F 2/18* (2006.01)
(Continued)

(52) U.S. Cl.
CPC .............. *H04R 25/30* (2013.01); *A61F 2/18* (2013.01); *A61N 1/36032* (2013.01);
(Continued)

(58) Field of Classification Search
CPC ................ H04R 25/556; H04R 25/602; H04R 25/00–25/75; H04R 2225/00–2225/83;
(Continued)

(56) References Cited

U.S. PATENT DOCUMENTS 5,164,652 A * 11/1992 Johnson .............. H01M 6/5066
320/106
5,602,455 A * 2/1997 Stephens ............... H02J 7/0013
320/106
(Continued)

FOREIGN PATENT DOCUMENTS

WO WO-2006/022645 3/2006
WO WO-2006/071210 7/2006

OTHER PUBLICATIONS

International Search Report and Written Opinion received in International Application No. PCT/US13/021604, dated Jan. 31, 2014.
(Continued)

*Primary Examiner* — Mark Fischer
(74) *Attorney, Agent, or Firm* — ALG Intellectual Property, LLC

(57) ABSTRACT

An exemplary sound processor apparatus included in an auditory prosthesis system includes 1) an interface assembly that includes at least a first contact, 2) a first switchable current source having an output coupled to the first contact of the interface assembly by way of a first data line, and 3) a control module that detects a connection of a battery module to the interface assembly by way of the first contact, enables the first switchable current source while the battery module is connected to the interface assembly, detects a logic level of the first data line while the first switchable current source is enabled and while the battery module is connected to the interface assembly, and identifies, based on the detected logic level of the first data line, a battery type (Continued)

associated with the battery module. Corresponding sound processor apparatuses, systems, and methods are also described.

18 Claims, 22 Drawing Sheets

(51) Int. Cl.
 *A61N 1/36* (2006.01)
 *A61N 1/372* (2006.01)
 *A61N 1/378* (2006.01)

(52) U.S. Cl.
 CPC .......... *A61N 1/37211* (2013.01); *A61N 1/378* (2013.01); *A61N 1/37252* (2013.01); *H04R 2225/61* (2013.01)

(58) Field of Classification Search
 CPC .. H02J 7/0004; H02J 7/0006; H02J 2007/006; H02J 2007/0062; H02J 2007/0098
 See application file for complete search history.

(56) References Cited

U.S. PATENT DOCUMENTS

| | | | | |
|---|---|---|---|---|
| 5,850,134 | A * | 12/1998 | Oh | H01M 10/42 320/106 |
| 6,014,008 | A * | 1/2000 | Hartzell | H02J 7/0006 320/106 |
| 6,144,748 | A | 11/2000 | Kerns | |
| 2004/0145487 | A1* | 7/2004 | Wendelrup | H02J 7/0004 340/636.1 |
| 2005/0174094 | A1* | 8/2005 | Purdy | H02J 7/0052 320/134 |
| 2005/0245991 | A1* | 11/2005 | Faltys | H04R 25/70 607/57 |
| 2007/0106344 | A1* | 5/2007 | Darley | A61N 1/36032 607/55 |
| 2009/0257610 | A1 | 10/2009 | Wu et al. | |
| 2010/0260367 | A1 | 10/2010 | Hasler et al. | |

OTHER PUBLICATIONS

Partial International Search Report received in International Application No. PCT/US13/021604, dated Aug. 29, 2013.

* cited by examiner

| Contact No. | Contact Name | Use Case |||||| 
| | | Normal Use | Normal Use, with audio enabled battery | Battery Charging | Listening Check | Device Fitting | R&D |
| --- | --- | --- | --- | --- | --- | --- | --- |
| | | Patient | Patient | Patient | Clinician | Clinician | R&D |
| 1 | GND | Power Ground | Power Ground | N/A | Power Ground | Power Ground | Power Ground |
| 2 | VB | Power Supply | Power Supply | Charge Supply | Power Supply | Power Supply | Power Supply |
| 3 | DPP− | Battery Type Detection (Digital Input) | Battery Type Detection (Digital Input) | Charger Ground (Rechargeable Cells Only) | Audio Output | Programming (input/output) | Any |
| 4 | DPP+ | Battery Type Detection (Digital Input) | Battery Type Detection (Digital Input) | Charger Ground (Rechargeable Cells Only) | Audio Output | Programming (input/output) | Any |
| 5 | AUX | Battery Model Detection | Audio Input + Battery Model Detection | Capacity Detection | Audio Input | Audio Input or EARB trigger output | Any |
| 6 | AUX_GND | N/A | Audio Ground | N/A | Audio Ground | Audio Ground | Audio Ground |
| 7 | AUX_PWR | N/A | Audio Supply | N/A | Audio Supply | Audio Supply | Audio Supply |
| 8 | DIO | N/A | N/A | Cell Temperature Sensor | N/A | N/A | Debug (Input/Output) |

SOUND PROCESSOR APPARATUSES THAT FACILITATE BATTERY TYPE DETECTION AND COMMUNICATION WITH A PROGRAMMING SYSTEM

BACKGROUND INFORMATION

Various types of auditory prosthesis systems have been developed to assist patients who have severe (e.g., complete) hearing loss. For example, cochlear implant systems may provide a sense of hearing for sensorineural hearing loss patients by providing electrical stimulation representative of sound directly to stimulation sites within the cochlea. As another example, electro-acoustic stimulation ("EAS") systems may assist patients with some degree of residual hearing in the low frequencies (e.g., below 1000 Hz) by providing acoustic stimulation representative of low frequency audio content and electrical stimulation representative of high frequency content.

Many auditory prosthesis systems include a sound processor apparatus (e.g., a behind-the-ear ("BTE") sound processing unit, a body worn device, etc.) configured to be located external to the patient. The sound processor apparatus may perform a variety of functions, such as processing audio signals presented to the patient, controlling an operation one or more implantable devices (e.g., one or more cochlear implants), and providing power to the one or more implantable devices.

A conventional sound processor apparatus may include an interface assembly that includes a plurality of contacts (e.g., a plurality of pins). One or more accessories and/or other types of external components may be connected to the sound processor apparatus by way of the interface assembly. Each contact included in the interface assembly is associated with a single dedicated function. For example, a particular contact may be used by the sound processor apparatus to receive programming data from a programming system while the programming system is connected to the sound processor apparatus by way of the interface assembly. However, the same contact may not be used to perform any other type of function while other types of external components (e.g., battery modules) are connected to the sound processor apparatus by way of the interface assembly.

Unfortunately, this limitation requires the use of an interface assembly that has a relatively large number of contacts (e.g., ten or more) in implementations where it is desirable for the sound processor apparatus to interchangeably connect to multiple external components. A high contact count necessarily increases the required physical size of the interface assembly, which in turn makes the sound processor apparatus undesirably large, bulky, and aesthetically unappealing.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 21 shows a table that lists a number of use cases and how each contact included in an eight contact interface assembly may be used by a control module in each use case according to principles described herein.

DETAILED DESCRIPTION

Figure 1:
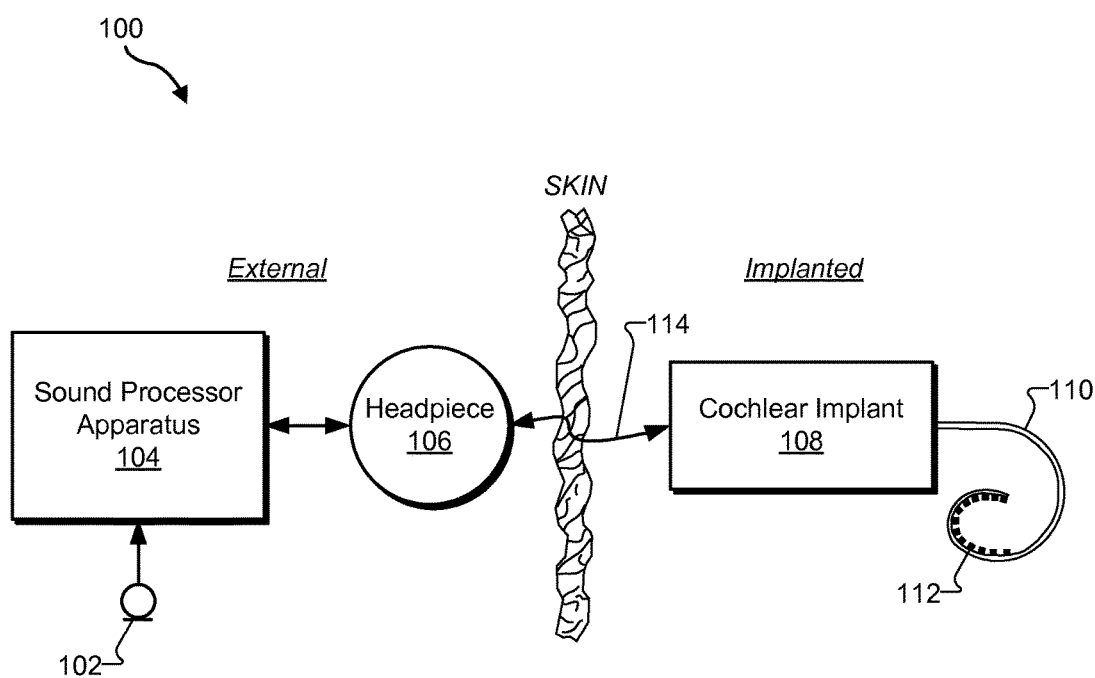
FIG. 1 illustrates an exemplary auditory prosthesis system according to principles described herein.

Sound processor apparatuses that facilitate battery type detection and communication with a programming system by way of the same contact(s) included in an interface assembly are described herein. As will be described below, an exemplary sound processor apparatus may include 1) an interface assembly that includes at least a first contact and a second contact and that facilitates interchangeable connectivity of a plurality of external components to the sound processor apparatus (e.g., by interchangeably connecting to the plurality of external components), and 2) a control module coupled to the first and second contacts and configured to selectively operate in a battery type detection mode and in a programming mode. While operating in the battery type detection mode, the control module uses the first and second contacts to detect a battery type of a battery module connected to the interface assembly. While operating in the programming mode, the control module uses the same first and second contacts to communicate with a programming system connected to the interface assembly.

To illustrate, while a battery module is connected to the interface assembly, the control module may use two contacts included in the interface assembly to identify a battery type associated with the battery module (e.g., whether the battery module includes a Lithium-Ion ("Li-Ion") battery or a Zinc-Air ("Zn-Air") battery). A user may then disconnect the battery module from the interface assembly and connect a programming cable associated with a programming system to the interface assembly in place of the battery module.

While the programming system is connected to the interface assembly, the control module may use the same two contacts to communicate with the programming system (e.g., in accordance with a differential signaling heuristic).

By overloading contacts with multiple functions in this manner (i.e., by using the same contact to perform different operations with respect to different external components coupled to the interface assembly), various benefits may be realized. For example, the number of contacts required to be included in the interface assembly for the sound processor apparatus to interact with multiple external components may be reduced compared to interface assemblies included in conventional sound processor apparatuses. This, in turn, may facilitate a lighter, less bulky, and more aesthetically pleasing sound processor apparatus. Furthermore, by overloading contacts with multiple functions, the sound processor apparatus described herein may interact with more external components and perform more operations with respect to the external components compared to conventional sound processor apparatuses.

Another exemplary sound processor apparatus described herein may include an interface assembly that includes a plurality of contacts and that facilitates interchangeable connectivity of a plurality of external components to the sound processor apparatus, a first switchable current source having an output coupled to the first contact of the interface assembly by way of a first data line, and a control module communicatively coupled to the first switchable current source and to the first data line and that 1) detects a connection of a battery module to the interface assembly by way of the first contact, 2) enables the first switchable current source while the battery module is connected to the interface assembly, 3) detects a logic level of the first data line while the first switchable current source is enabled and while the battery module is connected to the interface assembly, and 4) identifies, based on the detected logic level of the first data line, a battery type associated with the battery module.

By identifying the battery type associated with a battery module connected to the interface assembly, the control module may optimize a manner in which the sound processor apparatus operates. For example, the control module may determine a remaining battery life associated with the battery module and notify the patient accordingly, adjust one or more control parameters associated with the auditory prosthesis system (e.g., reduce the amplitude of the electrical stimulation being applied by a cochlear implant in order to optimize battery usage), determine when to initiate a shut down procedure of the sound processor apparatus (e.g., a safe shut down procedure when battery life is almost depleted), and/or perform any other operation as may serve a particular implementation.

FIG. 1 illustrates an exemplary auditory prosthesis system 100. Auditory prosthesis system 100 may include a microphone 102, a sound processor apparatus 104, a headpiece 106 having a coil disposed therein, a cochlear implant 108, and a lead 110 with a plurality of electrodes 112 disposed thereon. Additional or alternative components may be included within auditory prosthesis system 100 as may serve a particular implementation.

As shown, auditory prosthesis system 100 may include various components configured to be located external to a patient including, but not limited to, a microphone 102, a sound processor apparatus 104, and a headpiece 106. Auditory prosthesis system 100 may further include various components configured to be implanted within the patient including, but not limited to, a cochlear implant 108 and a lead 110 with a plurality of electrodes 112 disposed thereon. As will be described in more detail below, additional or alternative components may be included within auditory prosthesis system 100 as may serve a particular implementation. The components shown in FIG. 1 will now be described in more detail.

Microphone 102 may be configured to detect audio signals presented to the patient. Microphone 102 may be implemented in any suitable manner. For example, microphone 102 may include a "T-Mic" or the like that is configured to be placed within the concha of the ear near the entrance to the ear canal. Such a microphone may be held within the concha of the ear near the entrance of the ear canal by a boom or stalk that is attached to an ear hook configured to be selectively attached to sound processor apparatus 104. Additionally or alternatively, microphone 102 may be implemented by one or more microphones disposed within headpiece 106, one or more microphones disposed within sound processor apparatus 104, and/or any other suitable microphone as may serve a particular implementation.

Sound processor apparatus 104 (i.e., one or more components included within sound processor apparatus 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor apparatus 104 may process the one or more audio signals in accordance with a selected sound processing strategy or program to generate appropriate stimulation parameters for controlling cochlear implant 108. Sound processor apparatus 104 may include or be implemented by a behind-the-ear ("BTE") unit, a body worn device, and/or any other sound processing unit as may serve a particular implementation.

In some examples, sound processor apparatus 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bi-directional communication link and/or one or more dedicated uni-directional communication links.

Headpiece 106 may be communicatively coupled to sound processor apparatus 104 and may include an external antenna (e.g., a coil and/or one or more wireless communication components) configured to facilitate selective wireless coupling of sound processor apparatus 104 to cochlear implant 108. Headpiece 106 may be additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor apparatus 104 and cochlear implant 108 via a communication link 114 (which may include a bi-directional communication link and/or one or more dedicated uni-directional communication links as may serve a particular implementation.

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of cochlear implant that may be implanted within a patient and configured to apply stimulation to one or more stimulation sites located along an auditory pathway of a patient.

In some examples, cochlear implant 108 may be configured to generate electrical stimulation representative of an audio signal processed by sound processor apparatus 104 (e.g., an audio signal detected by microphone 102) in accordance with one or more stimulation parameters transmitted thereto by sound processor apparatus 104. Cochlear implant 108 may be further configured to apply the electrical stimulation to one or more stimulation sites within the patient via one or more electrodes 112 disposed along lead 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

Figure 2:
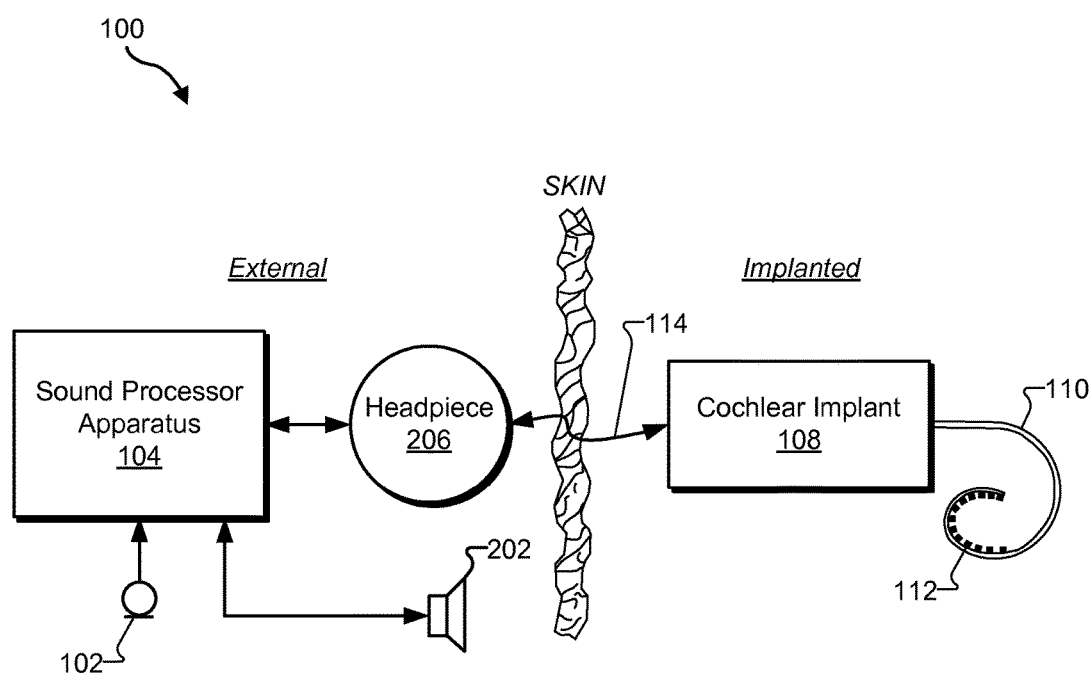
FIG. 2 illustrates an implementation of the auditory prosthesis system of FIG. 1 according to principles described herein.

The auditory prosthesis system 100 illustrated in FIG. 1 may be referred to as a cochlear implant system because sound processor apparatus 104 is configured to direct cochlear implant 108 to generate and apply electrical stimulation representative of audio content (e.g., one or more audio signals) to one or more stimulation sites within the patient by way of one or more of electrodes 112. FIG. 2 illustrates another implementation of auditory prosthesis system 100 in which auditory prosthesis system 100 is further configured to provide acoustic stimulation to the patient. Hence, the implementation shown in FIG. 2 may be referred to as an electro-acoustic stimulation ("EAS") system.

As shown, auditory prosthesis system 100 may further include a receiver 202 (also referred to as a loudspeaker). In this configuration, sound processor apparatus 104 may be configured to direct receiver 202 to apply acoustic stimulation representative of audio content included in a relatively low frequency band (e.g., below 1000 Hz) to the patient and cochlear implant 108 to apply electrical stimulation representative of audio content included in a relatively high frequency band (e.g., above 1000 Hz) to one or more stimulation sites within the patient by way of one or more of electrodes 112.

Figure 3:
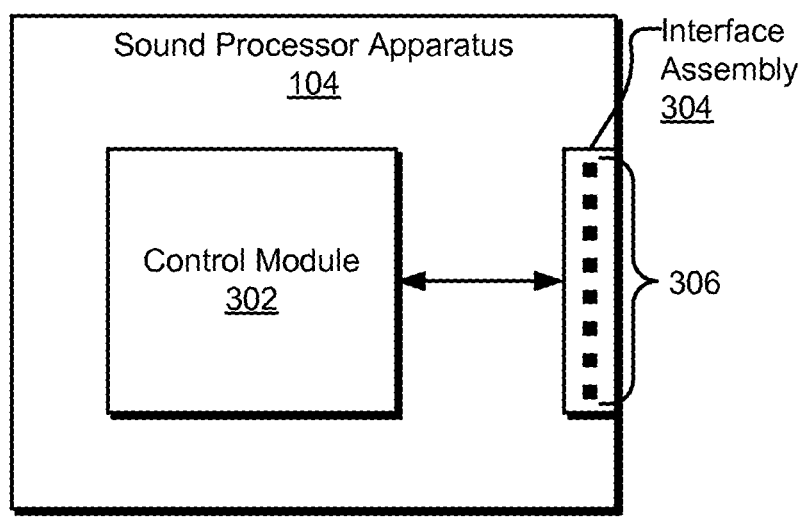
FIG. 3 illustrates exemplary components that may be included within a sound processor apparatus according to principles described herein.

FIG. 3 illustrates exemplary components that may be included within sound processor apparatus 104. As shown, sound processor apparatus 104 may include a control module 302 and an interface assembly 304 (also referred to as a "multipurpose interface assembly") that includes a plurality of contacts 306. It will be recognized that sound processor apparatus 104 may include additional or alternative components as may serve a particular implementation. In some examples, one or more of the components included in sound processor apparatus 104 (e.g., control module 302 and interface assembly 304) may be housed within a single casing.

Control module 302 may be configured to perform one or more operations with respect to one or more components connected to or otherwise communicative coupled to sound processor apparatus 104. For example, control module 302 may be configured to control an operation of cochlear implant 108, receiver 202, and/or any other device associated with providing electrical and/or acoustic stimulation to a patient. To illustrate, control module 302 may process an audio signal presented to the patient, generate one or more stimulation parameters based on the processing of the audio signal, and direct cochlear implant 108 to generate and apply electrical stimulation representative of the audio signal to the patient in accordance with the stimulation parameters (e.g., by transmitting the stimulation parameters to cochlear implant 108).

Control module 302 may be additionally or alternatively configured to interact with one or more external components connected to sound processor apparatus 104 by way of interface assembly 304. To this end, control module may overload at least some of contacts 306 with a plurality of functions. Exemplary manners in which this may be performed will be described below. Other ways in which control module 302 may overload at least some of contacts 305 with a plurality of functions are described in more detail in co-pending PCT Application No. PCT/US13/21605, entitled "Sound Processor Apparatuses with a Multipurpose Interface Assembly for Use in an Auditory Prosthesis System," filed the same day as the present application, and incorporated herein by reference in its entirety.

Control module 302 may be implemented by any suitable combination of integrated circuits, circuitry, processors, and/or computing devices configured to perform one or more of the operations and/or functions described herein. Exemplary implementations of control module 302 will be described below.

Interface assembly 304 may be configured to facilitate interchangeable connectivity of a plurality of external components to sound processor apparatus 104. To this end, interface assembly 304 may include a plurality of contacts 306. The number of contacts 306 may vary as may serve a particular implementation. For example, in some implementations, interface assembly 304 may include no more than eight contacts 306.

Each contact 306 may include any type of conductive contact (e.g., a male contact such as a pin or a female contact such as a receptacle) as may serve a particular implementation. Each contact 306 may be configured to be electrically coupled to a corresponding contact included in an interface assembly associated with (e.g., integrated into and/or otherwise coupled to) an external component while the external component is connected to interface assembly 304.

Figure 4:
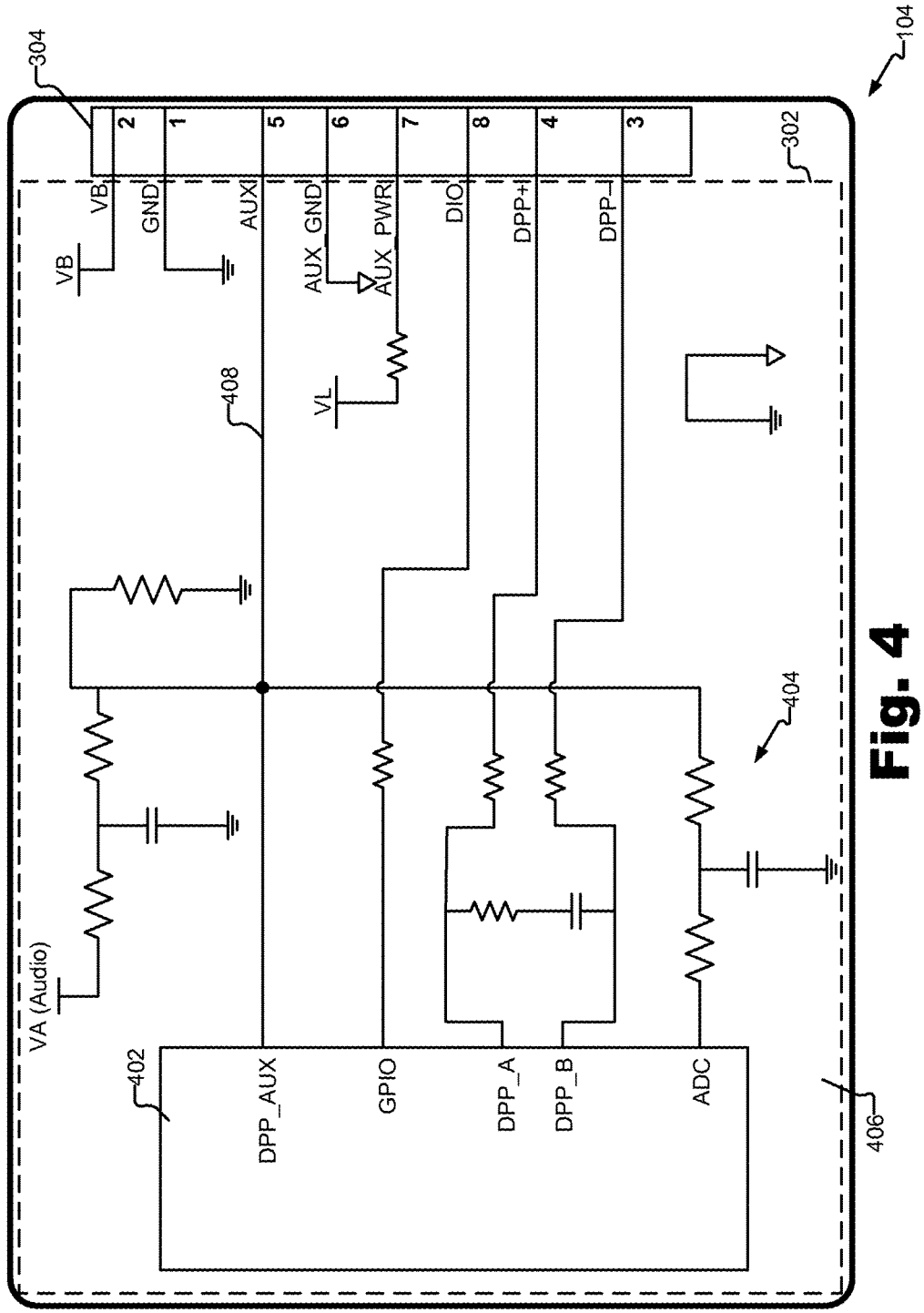
FIG. 4 shows an exemplary configuration of the sound processor apparatus of FIG. 3 according to principles described herein.

Control module 302 and interface assembly 304 may be implemented in any suitable manner. For example, FIG. 4 shows an exemplary configuration of sound processor apparatus 104 wherein control module 302 is implemented by an integrated circuit ("IC") 402 and various on-board electrical components 404 (e.g., resistors, capacitors, and grounds—the value of which may be selected as may best serve a particular implementation) disposed on a printed circuit board 406.

IC 402 may be implemented by any suitable combination of integrated circuits as may serve a particular implementation. IC 402 may include a plurality of ports. For example, as shown in FIG. 4, IC 402 may include an auxiliary port (DPP_AUX), a number of general purpose input/output ports labeled (GPIO), differential signaling ports (DPP_A and DPP_B), and an analog-to-digital port (ADC). Additional or alternative ports may be included in IC 402 as may serve a particular implementation.

In this particular implementation, interface assembly 304 has eight contacts, each of which may be connected to IC 402 and/or one or more electrical components 404 by way of one or more data lines (e.g., data line 408). The eight contacts are labeled 1 through 8 and named GND, VB, DPP−, DPP+, AUX_IN/TRIG, AUX_GND, V_AUX, and DIO, respectively.

Figure 5:
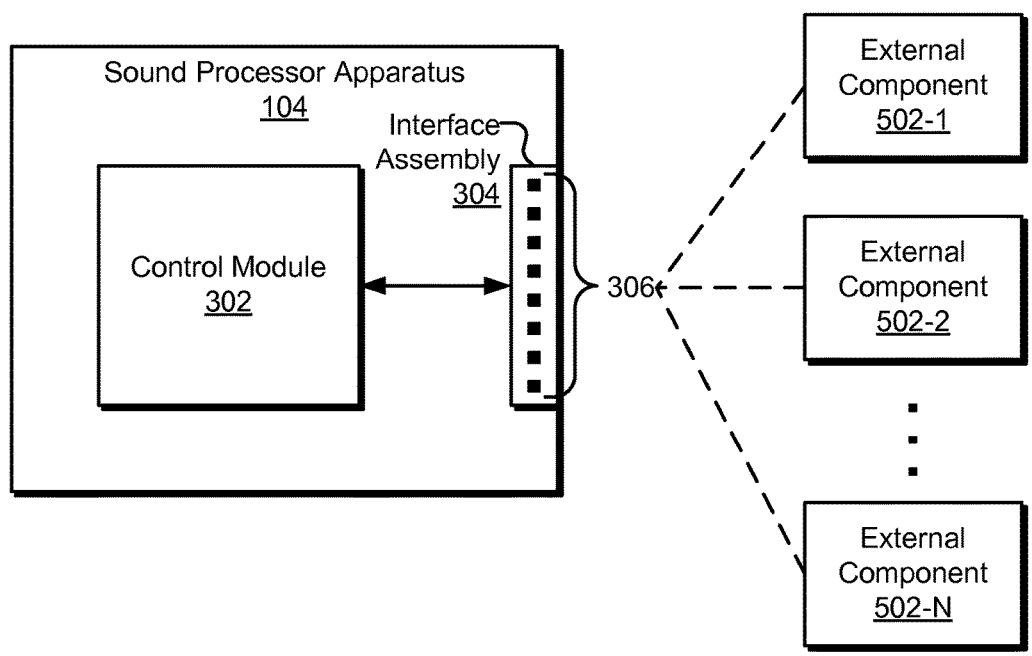
FIG. 5 shows that multiple external components may be interchangeably connected to an interface assembly of a sound processor apparatus according to principles described herein.

FIG. 5 shows that multiple external components 502 (e.g., external components 502-1 through 502-N) may be interchangeably connected to interface assembly 304 of sound processor apparatus 104 by way of contacts 306. Exemplary external components 502 include, but are not limited to, various types of battery modules (e.g., a rechargeable battery module such as a Li-Ion battery module, a non-rechargeable battery module such as a Zn-Air battery module, an audio-enabled battery module (e.g., a battery module that has an audio receiver connected thereto), etc.), a programming system (e.g., a fitting device), a listening check interposer, an audio receiver (e.g., a digital modulation ("DM") receiver), an off-ear power module, and/or any other type of external component as may serve a particular implementation.

In some examples, only a single external component 502 may be connected to sound processor apparatus 104 by way of interface assembly 304 at any given time. In other examples, multiple external components 502 may be concurrently connected to sound processor apparatus 104 by way of interface assembly 304. For example, a listening check interposer may be connected directly to interface assembly 304 and a battery module may be connected to the listening check interposer.

Various external components 502 that may be interchangeably connected to sound processor apparatus 104 by way of interface assembly 304 will now be described in connection with FIGS. 6-10. It will be recognized that the external components 502 described in connection with FIGS. 6-10 are merely illustrative of the many different external components that may be connected to sound processor apparatus 104 by way of interface assembly 304 in accordance with the systems and methods described herein. The external components 502 described in connection with FIGS. 6-10 may each be interchangeably connected to the eight-contact interface assembly 304 illustrated in FIG. 4.

Figure 6:
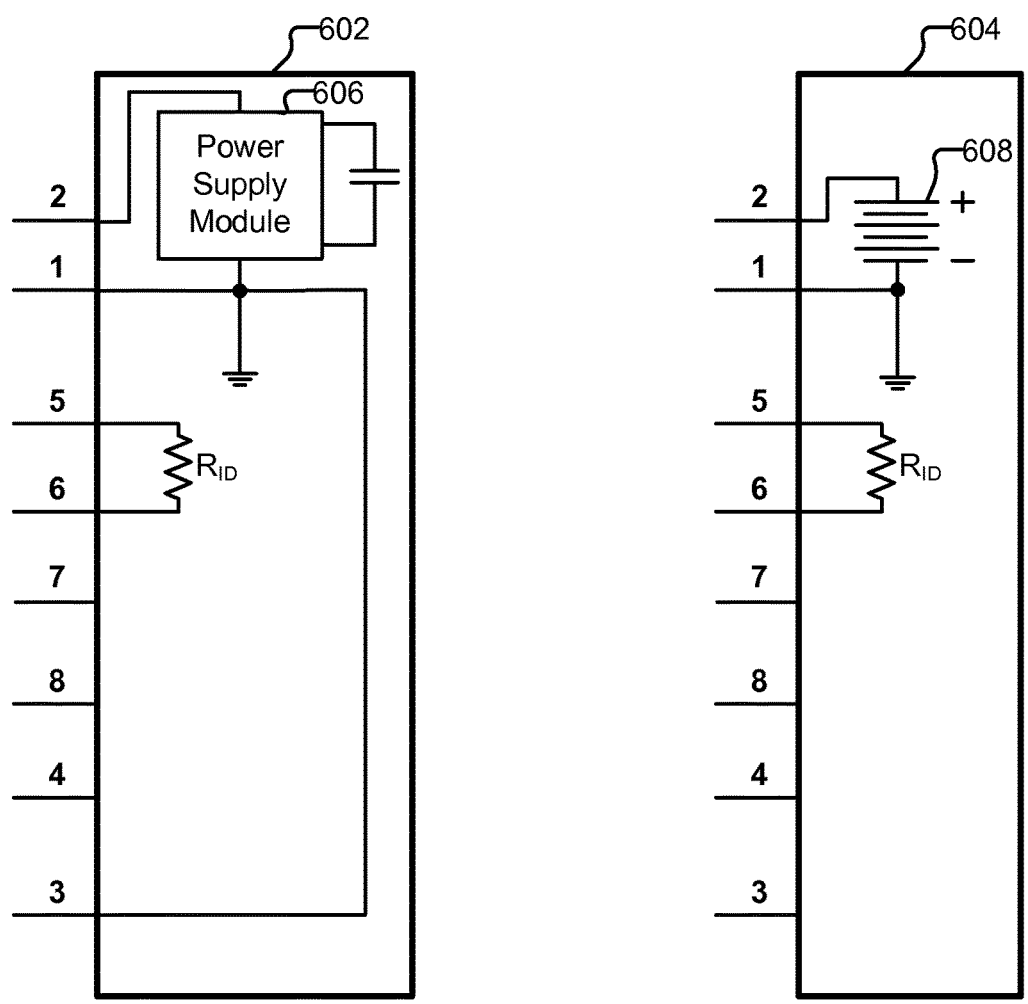
FIGS. 6-10 illustrate various external components that may be interchangeably connected to an interface assembly of a sound processor apparatus according to principles described herein.

FIG. 6 illustrates an exemplary Li-Ion battery module 602 and an exemplary Zn-Air battery module 604 that may each be interchangeably connected to interface assembly 304. As shown, each battery module 602 and 604 may include eight contacts (labeled 1 through 8) configured to be in communication with (i.e., make physical contact with) corresponding contacts 306 included in interface assembly 304.

Li-Ion battery module 602 may include a rechargeable power supply module 606 configured to provide power to sound processor apparatus 104 by way of contact 2 (with contact 1 being used as a power supply ground). An exemplary voltage range for the power provided by power supply module 606 is up to 4.2 volts DC ("VDC").

Zn-Air battery module 604 may include a non-rechargeable power supply 608 (e.g., a battery pack that includes one or more Zn-Air batteries) configured to provide power to sound processor apparatus 104 by way of contact 2 (with contact 1 being used as a power supply ground). An exemplary voltage range for the power provided by power supply 608 is up to 1.6 VDC per cell (e.g., 3.2 VDC in cases where Zn-Air battery module 604 includes two cells).

As shown, each battery module 602 and 604 may include a resistor $R_{ID}$ that bridges contacts 5 and 6. As will be described below, this resistor may be used by control module 302 of sound processor apparatus 104 to identify a battery model associated with each battery module 602 and 604. The value of resistor $R_{ID}$ (and all other resistors described herein) may be selected as may serve a particular implementation.

As also shown, contact 3 of Li-Ion battery module 602 may be connected to ground, while contact 3 of Zn-Air battery module 604 may be left open (i.e., not connected to anything). As will be described below, sound processor apparatus 104 may detect whether contact 3 of a battery module connected to interface assembly 304 is grounded or left open and identify a battery type associated with the battery module accordingly (e.g., whether the battery module is a Li-Ion battery module or a Zn-Air battery module).

As also shown, various contacts (e.g., contacts 4, 7, and 8 of Li-Ion battery module 602 and contacts 3, 4, 7, and 8 of Zn-Air battery module 604) may be left open.

Figure 7:
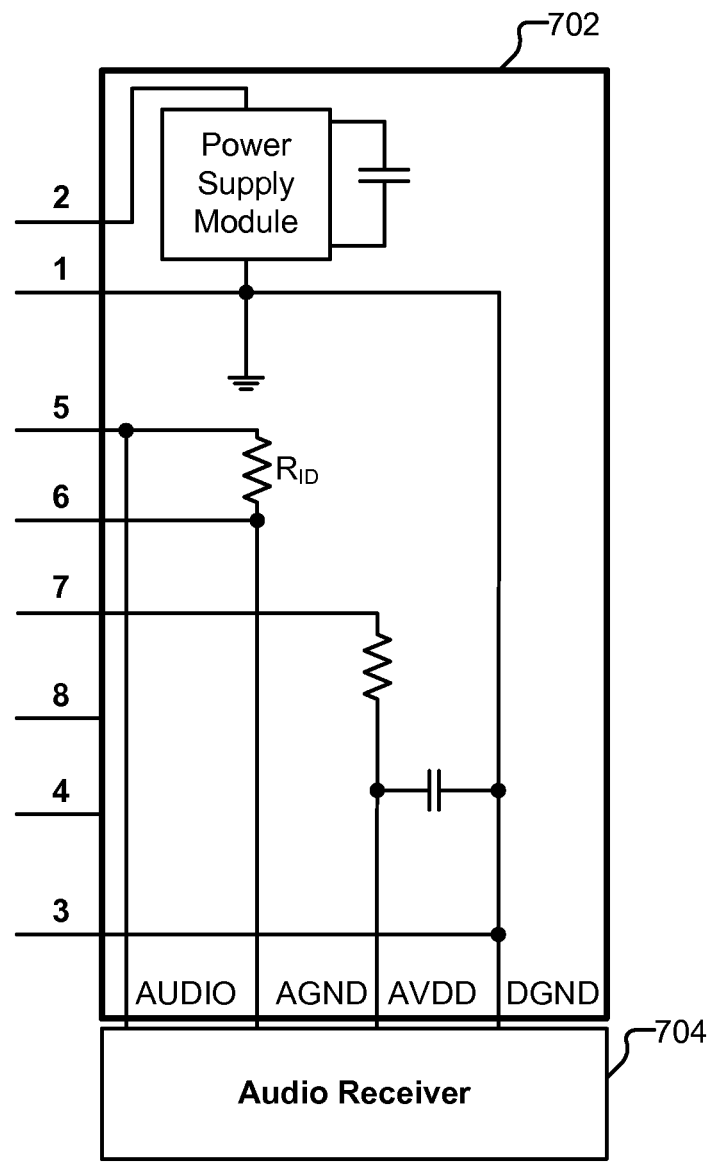

FIG. 7 illustrates an exemplary audio-enabled battery module 702 that may be interchangeably connected to interface assembly 304. As shown, audio-enabled battery module 702 may include eight contacts (labeled 1 through 8) configured to be in communication with (i.e., make physical contact with) corresponding contacts 306 included in interface assembly 304 while audio-enabled battery module 702 is connected to interface assembly 304.

Audio-enabled battery module 702 is similar to Li-Ion battery module 602 in that it includes a rechargeable power supply module 606 configured to provide power to sound processor apparatus 104 by way of contact 2 (with contact 1 being used as a power supply ground) and a resistor $R_{ID}$ that bridges contacts 5 and 6. Alternatively, audio-enabled battery module 702 may include a Zn-Air power supply.

As shown, audio-enabled battery module 702 includes an audio receiver 704 (e.g., an FM or DM receiver) coupled to contacts 1, 3, 5, 6, and 7. Audio receiver 704 may be configured to provide audio input to sound processor apparatus 104 while audio-enabled battery module 702 is connected to interface assembly 304. Contacts 4 and 8 may be left open.

Figure 8:
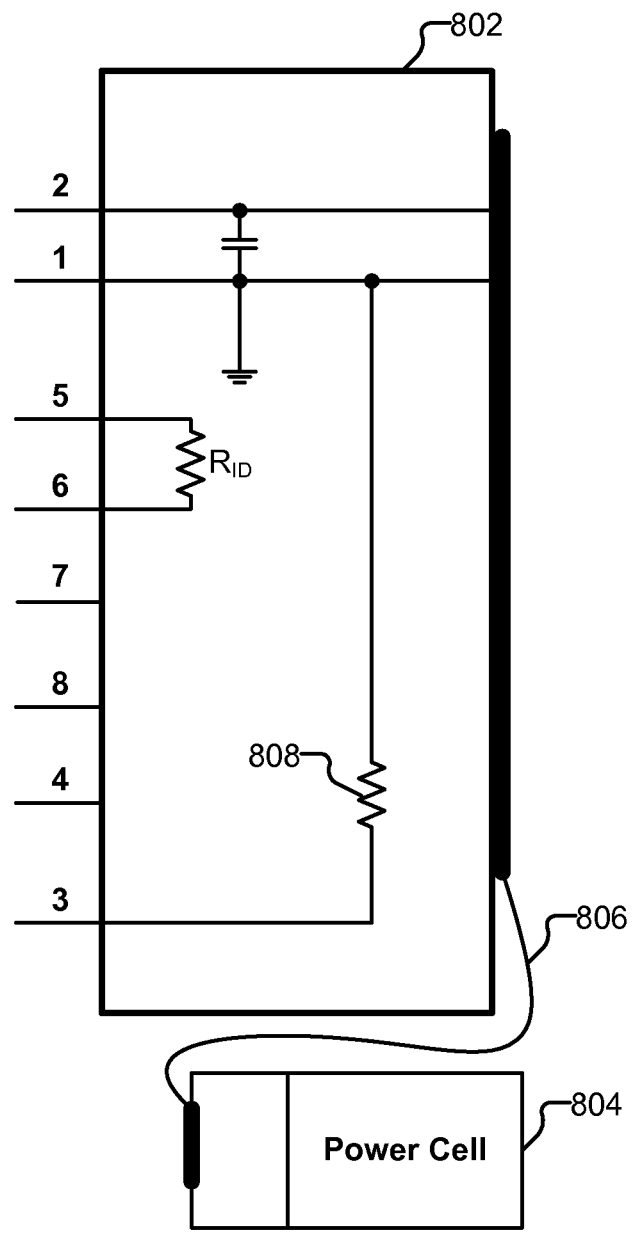

FIG. 8 illustrates an exemplary off-ear power module 802 that may be interchangeably connected to interface assembly 304. As shown, off-ear power module 802 may include eight contacts (labeled 1 through 8) configured to be in communication with (i.e., make physical contact with) corresponding contacts 306 included in interface assembly 304 while off-ear power module 802 is connected to interface assembly 304.

As shown, off-ear power module 802 may include a power cell 804 configured to be worn off the ear. Power cell 804 may use relatively large batteries (e.g., AAA batteries) and may be connected to contacts 1 and 2 by way of a cable 806 that includes, for example, two wires.

Off-ear power module 802 may also include a resistor 808 that bridges contact 3 and ground. Resistor 808 may prevent a charging device (described below) from charging (and hence, damaging) off-ear power module 802 if a user inadvertently inserts off-ear power module 802 into the charging device. Contacts 4, 7, and 8 may be left open.

Figure 9:
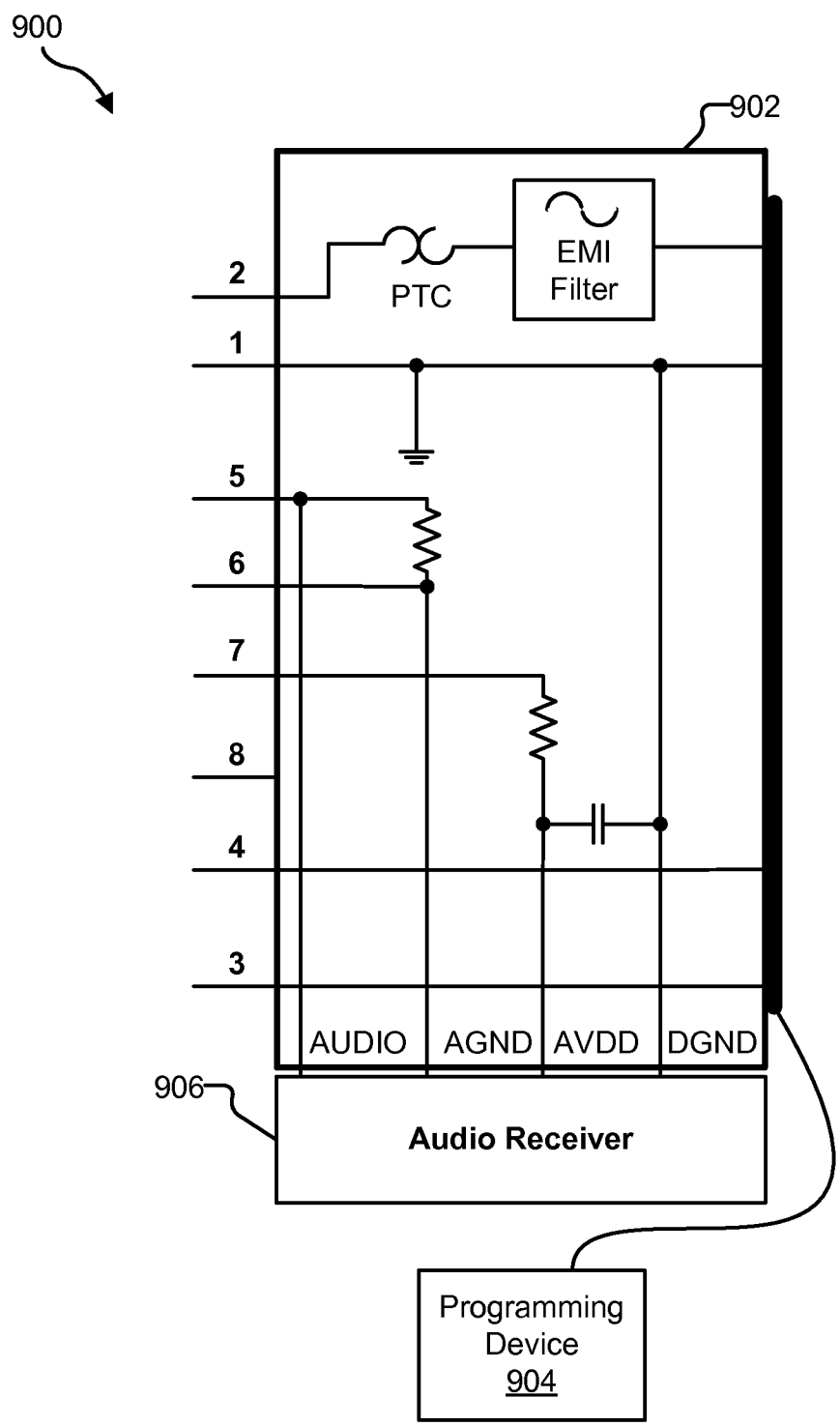

FIG. 9 illustrates an exemplary programming system 900 that may be interchangeably connected to interface assembly 304. As shown, programming system 900 may include a connection interface 902 coupled to a programming device 904.

Programming device 904 may include, but is not limited to, a fitting station, a personal computer, a laptop computer, a handheld device, a mobile device (e.g., a mobile phone), a clinician's programming interface ("CPI") device, and/or any other suitable device used to program sound processor apparatus 104 as may serve a particular implementation. Programming device 904 may be configured to communicate with (e.g., provide programming data to) sound processor apparatus 104 (i.e., control module 302), provide power to sound processor apparatus 104, and/or otherwise interact with sound processor apparatus 104 while programming system 902 is connected to interface assembly 304.

Connection interface 902 may be implemented, for example, by a programming cable, and may include eight contacts (labeled 1 through 8) configured to be in communication with (i.e., make physical contact with) corresponding contacts 306 included in interface assembly 304 while programming system 902 is connected to interface assembly 304.

As shown, an audio receiver 906 (e.g., an FM or DM receiver) may be coupled to connection interface 902 and configured to provide audio to sound processor apparatus 104 while programming system 902 is connected to interface assembly 304.

Figure 10:
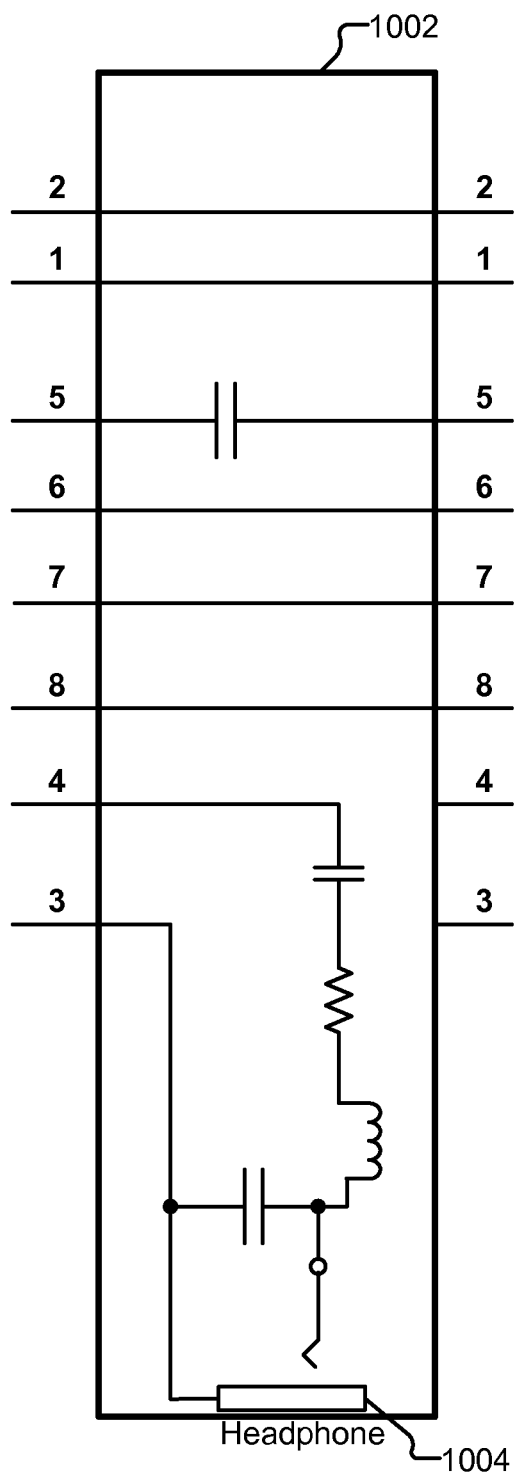

FIG. 10 illustrates an exemplary listening check interposer 1002 that may be interchangeably connected to interface assembly 304. As shown, listening check interposer 1002 may include eight contacts (labeled 1 through 8) configured to be in communication with (i.e., make physical contact with) corresponding contacts 306 included in interface assembly 304 while listening check interposer 1002 is connected to interface assembly 304.

Listening check interposer 1002 may be configured to allow a clinician or other user to listen to the audio that is being presented to the patient (e.g., audio detected by microphone 102, audio provided by an auxiliary audio input device, etc.). To this end, contacts 3 and 4 are connected to a headphone 1004, which may be used by the clinician or other user to listen to the audio. As shown, the contacts feed through listening check interposer 1002 so that a battery module or other suitable external component may be coupled to interface assembly 304 by way of listening check interposer 1002.

Listening check interposer 1002 is merely an example of the various interposers that may be connected to interface assembly 304 of sound processor apparatus 104. Other types of interposers (e.g., auxiliary audio interposers) may additionally or alternatively be connected to interface assembly 304.

As mentioned, control module 302 may overload one or more contacts 306 each with a plurality of functions in order to perform different operations with respect to the different external components illustrated in FIGS. 6-10 that may be coupled to interface assembly 304. At the same time, various contacts 306 may not be overloaded (i.e., they may be used for a single function regardless of the external component 502 connected to interface assembly 304).

Figure 11:
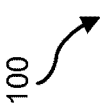
FIG. 11 shows a table that lists functions that may be assigned to each contact included in an interface assembly of a sound processor apparatus according to principles described herein.

For example, FIG. 11 shows a table 1100 that lists functions that may be assigned to each contact 306 included in interface assembly 304 (i.e., contacts 1 through 8 shown in FIG. 4) for each of the external components illustrated in FIGS. 6-10. The functions shown in table 1100 are merely illustrative of the many different functions that may be assigned to each contact 306.

As shown, contact 1 may serve as a power supply ground (BAT−) port for sound processor apparatus 104 regardless of which external component is connected to interface assembly 304. Likewise, contact 2 may serve as a power supply port (BAT+) regardless of which external component is connected to interface assembly 304. In some examples, sound processor apparatus 104 (i.e., control module 302) may be configured to tolerate up to a maximum voltage level (e.g., 5.5 VDC) on contact 2 with respect to the power supply ground on contact 1.

With reference still to table 1100, contacts 3 and 4 may be used by control module 302 to identify a battery type associated with a particular battery module (e.g., Li-Ion battery module 602, Zn-Air battery module 604, audio enabled battery module 702, and off-ear power module 802) while the battery module is connected to interface assembly 304. This function is referred to as "BAT ID−" and "BAT ID+" in table 1100.

Figure 12:
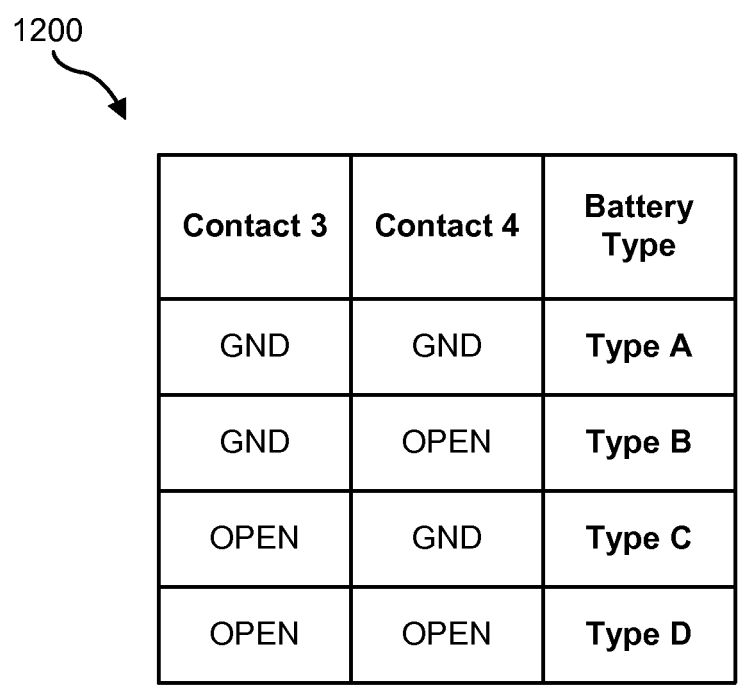
FIG. 12 shows a table that illustrates possible connection states that may be used to identify a battery type associated with a particular battery module that is connected to an interface assembly of a sound processor apparatus according to principles described herein.

To illustrate, FIG. 12 shows a table 1200 that illustrates possible connection states of contact 3 and contact 4 when a particular battery module is connected to interface assembly 304. A look-up table similar to table 1200 may be maintained and used by control module 302 to identify a battery type associated with a particular battery module connected to interface assembly 304.

As shown, each contact (i.e., contacts 3 and 4) may be either connected to ground or left open while a battery module is connected to interface assembly 304. To illustrate, with reference to FIG. 6, contact 3 is connected to ground while Li-Ion battery module 602 is connected to interface assembly 304 and left open when Zn-Air battery module 604 is connected to interface assembly 304. Because there are two possible connection states for each contact (i.e., contacts 3 and 4), a total of four different battery types (e.g., Type A through Type D shown in FIG. 12) may be identified by control module 302. Exemplary battery types include, but are not limited to, an Li-Ion battery type, a Zn-Air battery type, and/or any other battery type as may serve a particular implementation.

To illustrate, with respect to the various battery modules illustrated herein, contact 3 is connected to ground and contact 4 is left open while either Li-Ion battery module 602 or audio-enabled battery module 702 is connected to interface assembly 304. Hence, in accordance with table 1200, control module 302 may determine that both of these battery modules 602 and 702 are associated with a battery type of "Type B" (which, in this case, may be representative of a Li-Ion battery type). With respect to off-ear power module 802, contact 3 is also connected to ground (even though resistor 808 is present between contact 3 and ground) and contact 4 is left open while off-ear power module 802 is connected to interface assembly 304. Hence, in accordance with table 1200, control module 302 may determine that off-ear power module 802 is also associated with a battery type of "Type B".

As another example, contacts 3 and 4 are both left open while Zn-Air battery module 604 is connected to interface assembly 304. Hence, in accordance with table 1200, control module 302 may determine that Zn-Air battery module 604 is associated with a battery type of "Type D" (which, in this case, may be representative of a Zn-Air battery type).

Each battery type shown in FIG. 12 may correspond to a particular voltage range provided by the particular battery module connected to interface assembly 304. For example, Type B shown in FIG. 12 corresponds to a voltage range typically provided by a Li-Ion battery type (e.g., by Li-Ion battery module 602). As another example, Type D shown in FIG. 12 corresponds to a voltage range typically provided by a Zn-Air battery type (e.g., by Zn-Air battery module 602). Each voltage range may be different as may serve a particular implementation.

Exemplary manners in which control module 302 may determine whether contacts 3 and 4 are connected to ground or left open in order to identify a battery type associated with a battery module that is connected to interface assembly 304 will now be described in connection with FIGS. 13-16.

Figure 13:
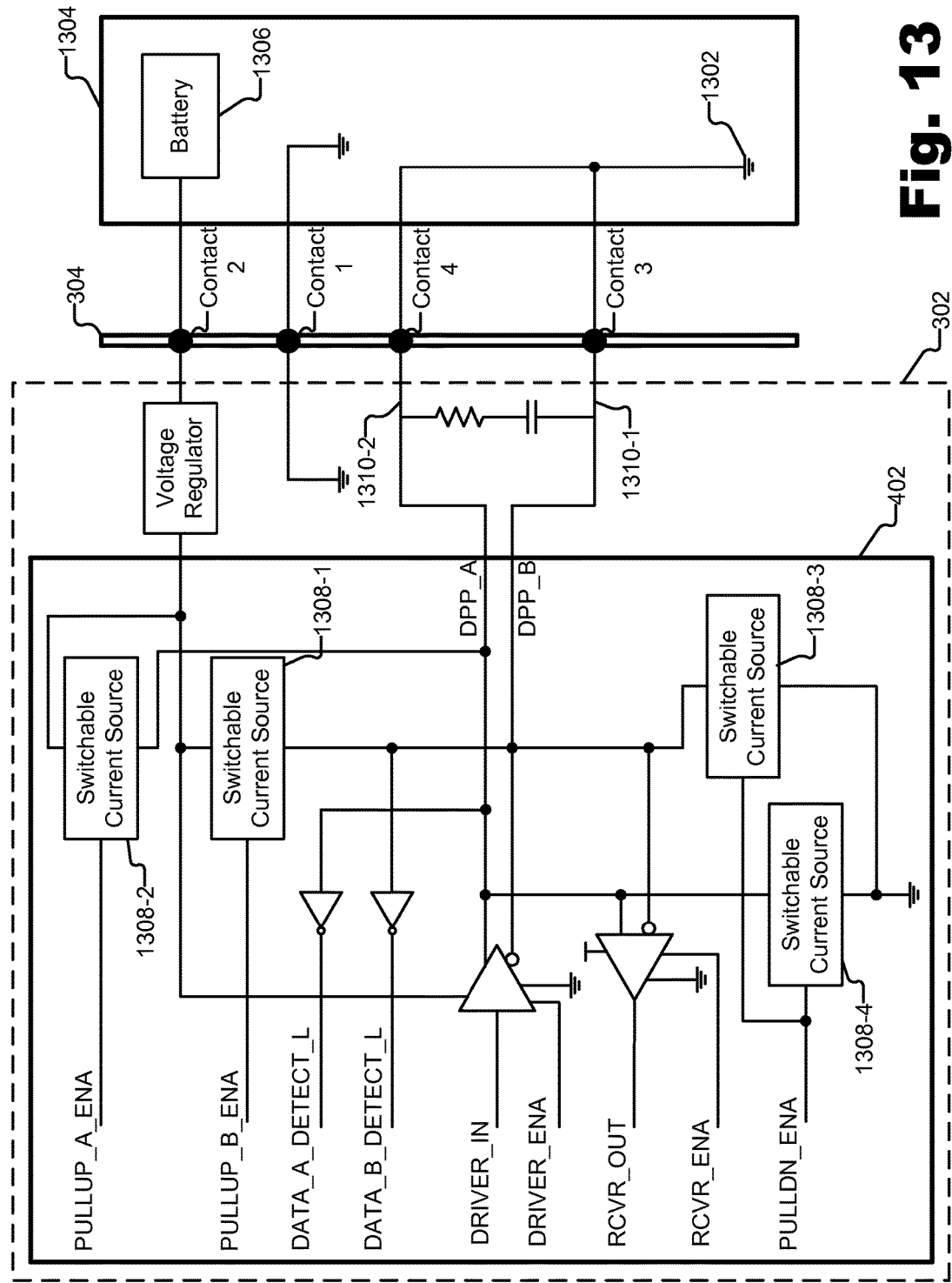
FIGS. 13-19 show various external components connected to an interface assembly of a sound processor assembly according to principles described herein.
Figure 14:
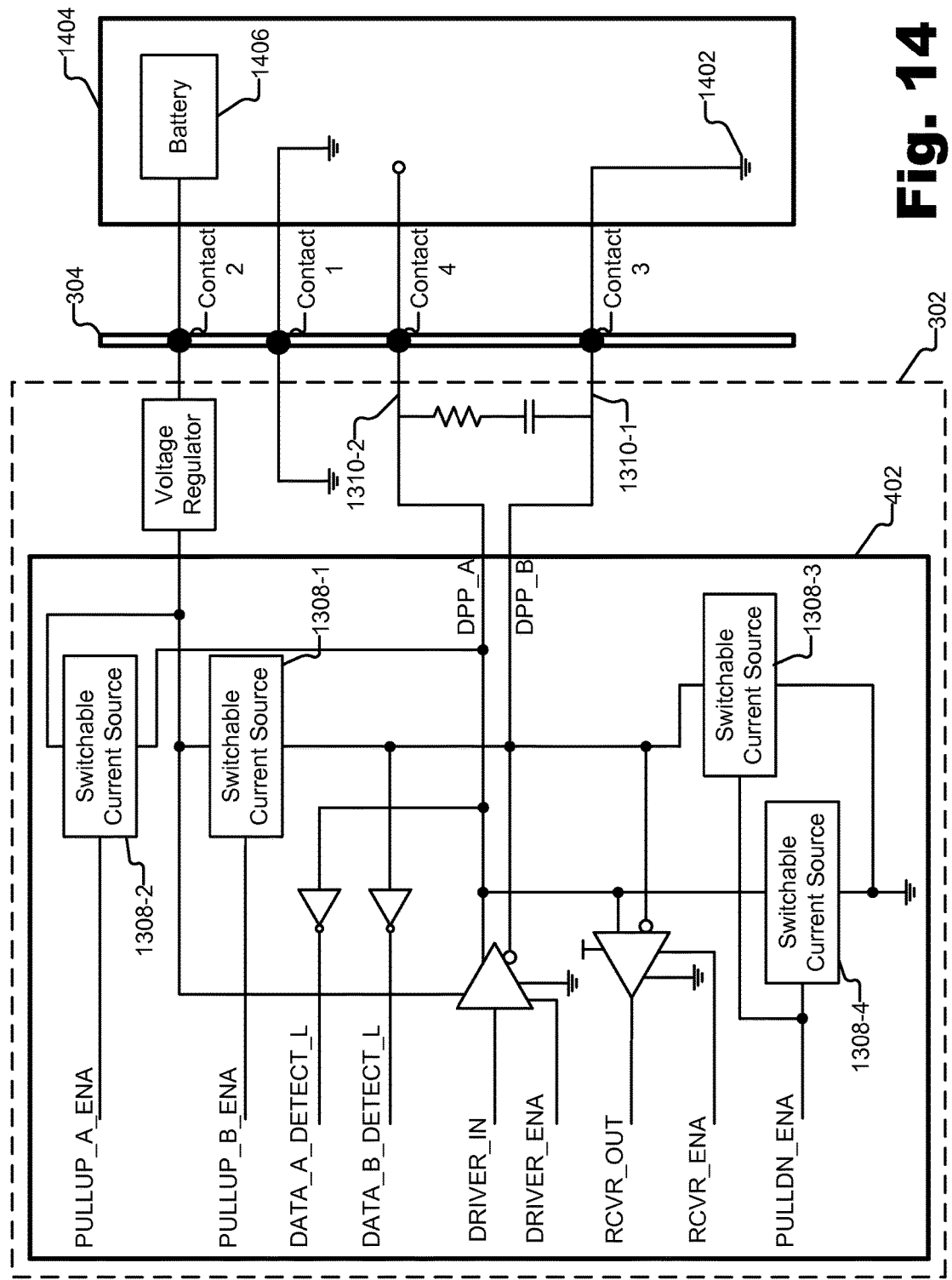
Figure 15:
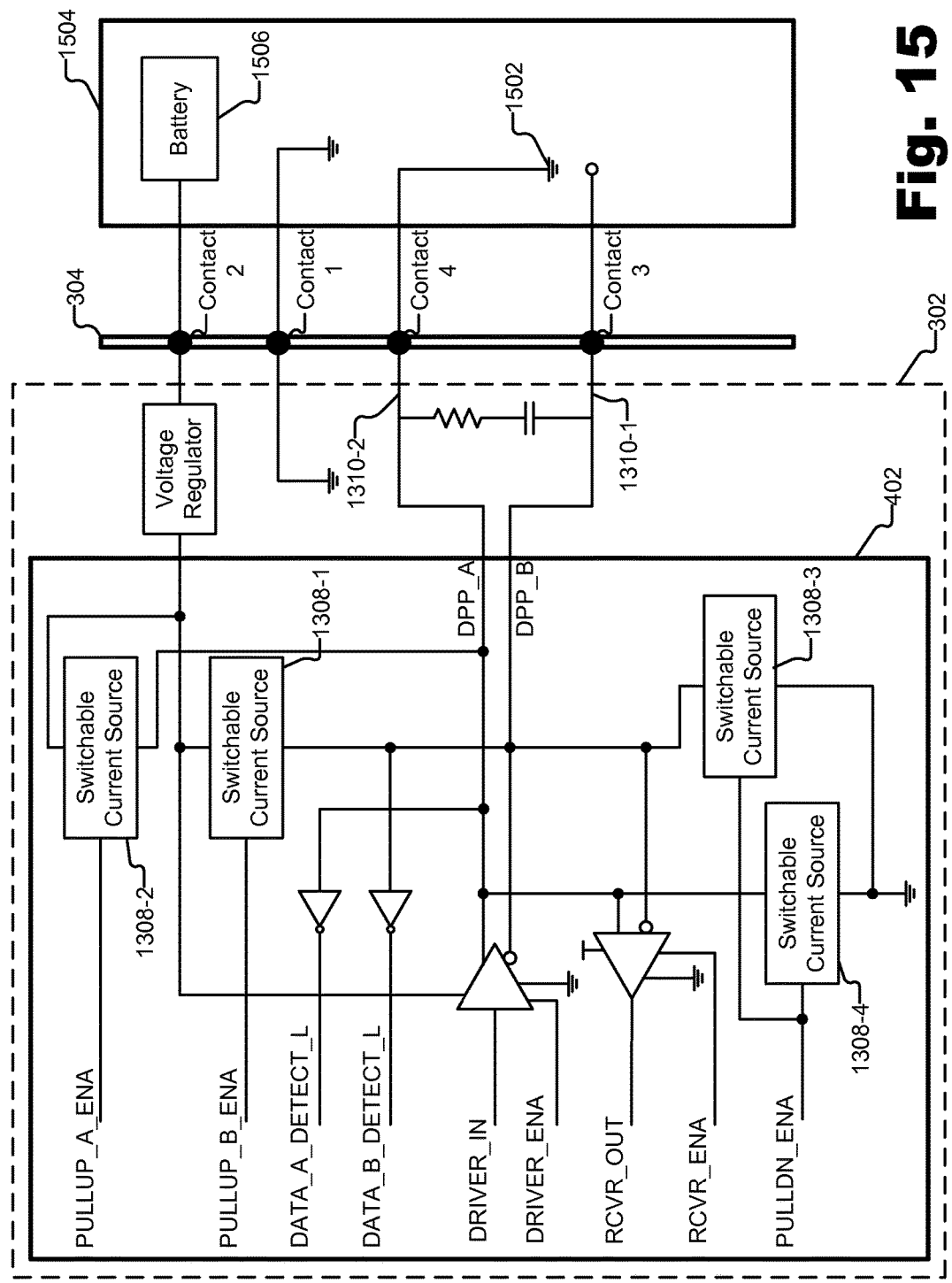
Figure 16:
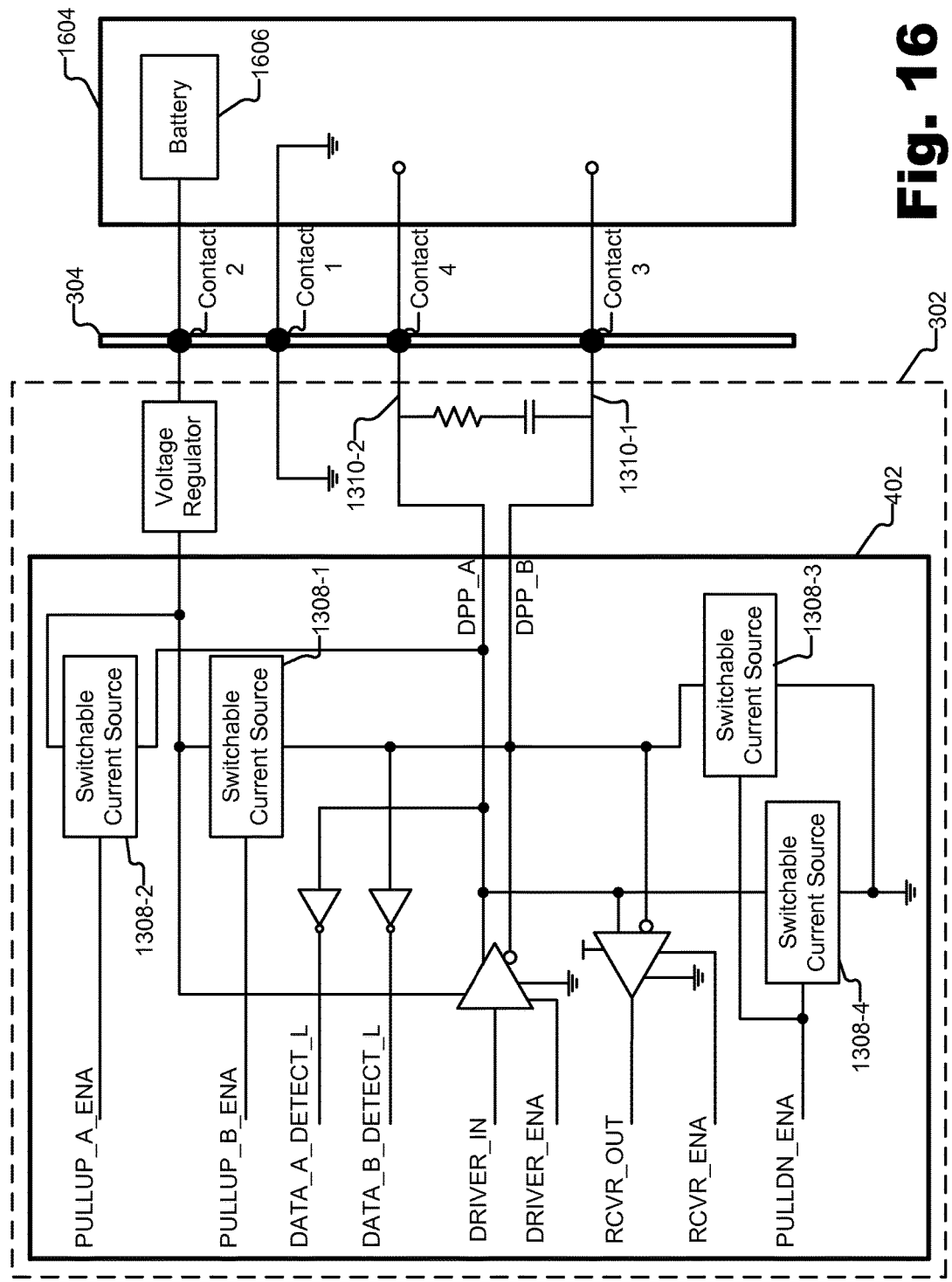

FIGS. 13-16 illustrate the various connection states shown in FIG. 12 of contacts 3 and 4 while various battery modules are connected to interface assembly 304. For example, FIG. 13 shows that contacts 3 and 4 are both connected to ground (i.e., ground 1302) while a first type of battery module 1304 is connected to interface assembly 304. FIG. 14 shows that contact 3 is connected to ground (i.e., ground 1402) and contact 4 remains open while a second type of battery module 1404 is connected to interface assembly 304. FIG. 15 shows that contact 3 remains open and contact 4 is connected to ground (i.e., ground 1502) while a third type of battery module 1504 is connected to interface assembly 304. FIG. 16 shows that both contacts 3 and 4 remain open while a fourth type of battery module 1604 is connected to interface assembly 304. As shown in FIGS. 13-16, each battery module 1302, 1402, 1502, and 1602 includes a battery 1306, 1406, 1506, and 1606, respectively, configured to provide power to control module 302 of sound processor assembly 104.

FIGS. 13-16 also show various components internal to IC 402 that may be used to determine a connection state of contacts 3 and 4 while a particular battery module (e.g., one of battery modules 1302, 1402, 1502, and 1602) is connected to interface assembly 304 (and therefore identify a battery type associated with the battery module. For example, IC 402 may include a plurality of switchable current sources 1308 (i.e., pull-up switchable current sources 1308-1 and 1308-2 and pull-down switchable current sources 1308-3 and 1308-4) as well as a number of logical components. Each switchable current source 1308 may be of any suitable size (e.g., 5 microamps) and implemented by any suitable current source and switch. As shown, the outputs of current sources 1308-1 and 1308-2 are coupled to contacts 3 and 4, respectively, by way of data lines 1310-1 and 1310-2, respectively.

To identify a battery type associated with a particular battery module, control module 302 (i.e., IC 402) may detect a connection of the battery module to interface assembly 304 (i.e., determine that the battery module is connected to interface facility 304. This may be performed in any suitable manner. For example, the detection may be performed during a powering on of sound processor apparatus 104 (e.g., during a boot sequence of sound processor apparatus 104). To illustrate, upon power reset, control module 302 may attempt to communicate with a programming system. If this communication is unsuccessful, control module 302 may assume that a battery module is connected. Additionally or alternatively, control module 302 may detect the connection of the battery module by detecting a voltage level change on a data line that occurs in response to the connection and/or in any other way as may serve a particular implementation.

Control module 302 may then enable (i.e., turn on) switchable current sources 1308-1 and 1308-2. Control module 302 may enable switchable current sources 1308-1 and 1308-2 in any suitable manner. For example, control module 302 may assert the lines labeled PULLUP_A_ENA and PULLUP_B_ENA in order to enable switchable current sources 1308-1 and 1308-2.

Control module 302 may detect a logic level of data lines 1310-1 and 1310-2 while switchable current sources 1308-1 and 1308-2 are enabled and then identify, based on the detected logic levels, a battery type associated with the battery module.

To illustrate, enablement of current source 1308-1 will pull data line 1310-1 to a logic high if contact 3 is open (i.e., not connected to ground). However, data line 1310-1 will not be pulled high (and therefore remain a logic low) if contact 3 is connected to ground. Likewise, enablement of current source 1308-2 will pull data line 1310-2 to a logic high if contact 4 is open (i.e., not connected to ground). However, data line 1310-2 will not be pulled high (and therefore remain a logic low) if contact 4 is connected to ground. Control module 302 may detect these logic levels (e.g., by detecting a logic level of DATA_A_DETECT_L and DATA_B_DETECT_L lines, which, in this configuration, will have logic levels opposite that of their corresponding data lines 1310-1 and 1310-2) and thereby identify a battery type associated with the battery module.

To illustrate, control module 302 may identify the battery type as being a first battery type (e.g., "Type A" shown in FIG. 12) if the detected logic level of data line 1310-1 and the detected logic level of data line 1310-2 are both logic lows (which would occur in the configuration shown in FIG. 13). Alternatively, control module 302 may identify the battery type as being a second battery type (e.g., "Type B" shown in FIG. 12) if the detected logic level of data line 1310-1 is a logic low and the detected logic level of data line 1310-2 is a logic high (which would occur in the configuration shown in FIG. 14). Alternatively, control module 302 may identify the battery type as being a third battery type (e.g., "Type C" shown in FIG. 12) if the detected logic level of data line 1310-1 is a logic high and the detected logic level of data line 1310-2 is a logic low ((which would occur in the configuration shown in FIG. 15). Alternatively, control module 302 may identify the battery type as being a fourth battery type (e.g., "Type D" shown in FIG. 12) if the detected logic level of data line 1310-1 and the detected logic level of data line 1310-2 are both logic highs (which would occur in the configuration shown in FIG. 16).

In some examples, switchable current sources 1308-1 and 1308-2 may be disabled by control module 304 in response to identifying the battery type associated with a battery module connected to interface assembly 304. In this manner, power utilized by current sources 1308-1 and 1308-2 may be conserved while control module 302 is not actively identifying the battery type. Control module 304 may disable switchable current sources 1308-1 and 1308-2, for example, by de-asserting the lines labeled PULLUP_A_ENA and PULLUP_B_ENA.

Figure 17:
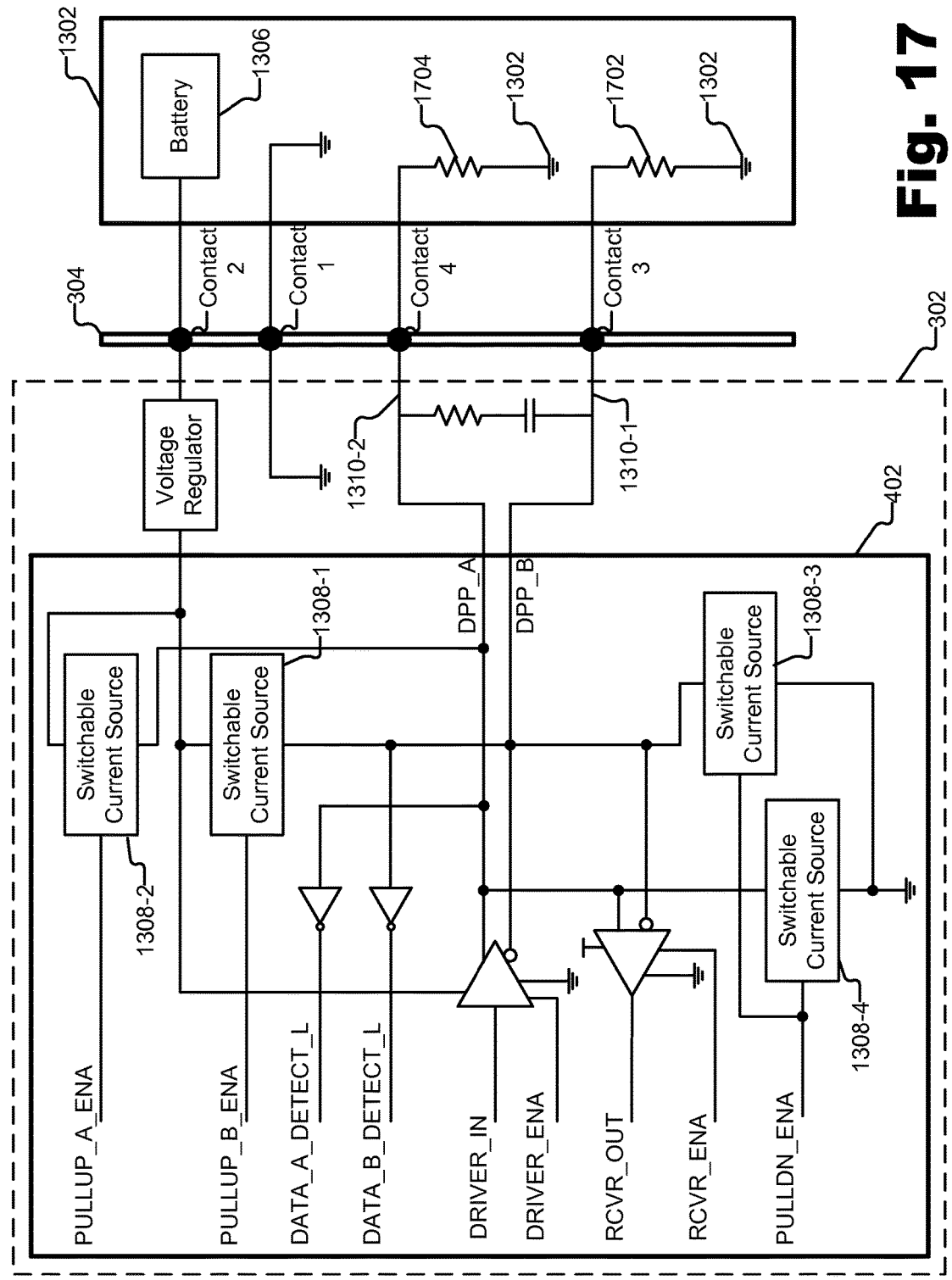

In some alternative embodiments, contacts 3 and/or 4 may be connected to ground by way of a resistor (e.g., a pull-down resistor). For example, FIG. 17 is similar to FIG. 13, except that both contacts 3 and 4 are connected to ground by way of a pull-down resistor (i.e., pull-down resistors 1702 and 1704, respectively). The value of pull-down resistors 1702 and 1704 may be any suitable value (e.g., 100 Kohms). In configurations such as that shown in FIG. 17, control module 302 may identify battery type associated with a battery module connected to interface assembly 304 in a similar manner as that described in connection with FIGS. 13-16.

It will be recognized that more or less contacts may be used to identify the battery type depending on the total number of battery types that it is desired for control module 302 to identify. For example, when it is desirable to only identify two different battery types, a single contact (e.g., contact 3) may be used instead of two contacts as described above.

Figure 18:
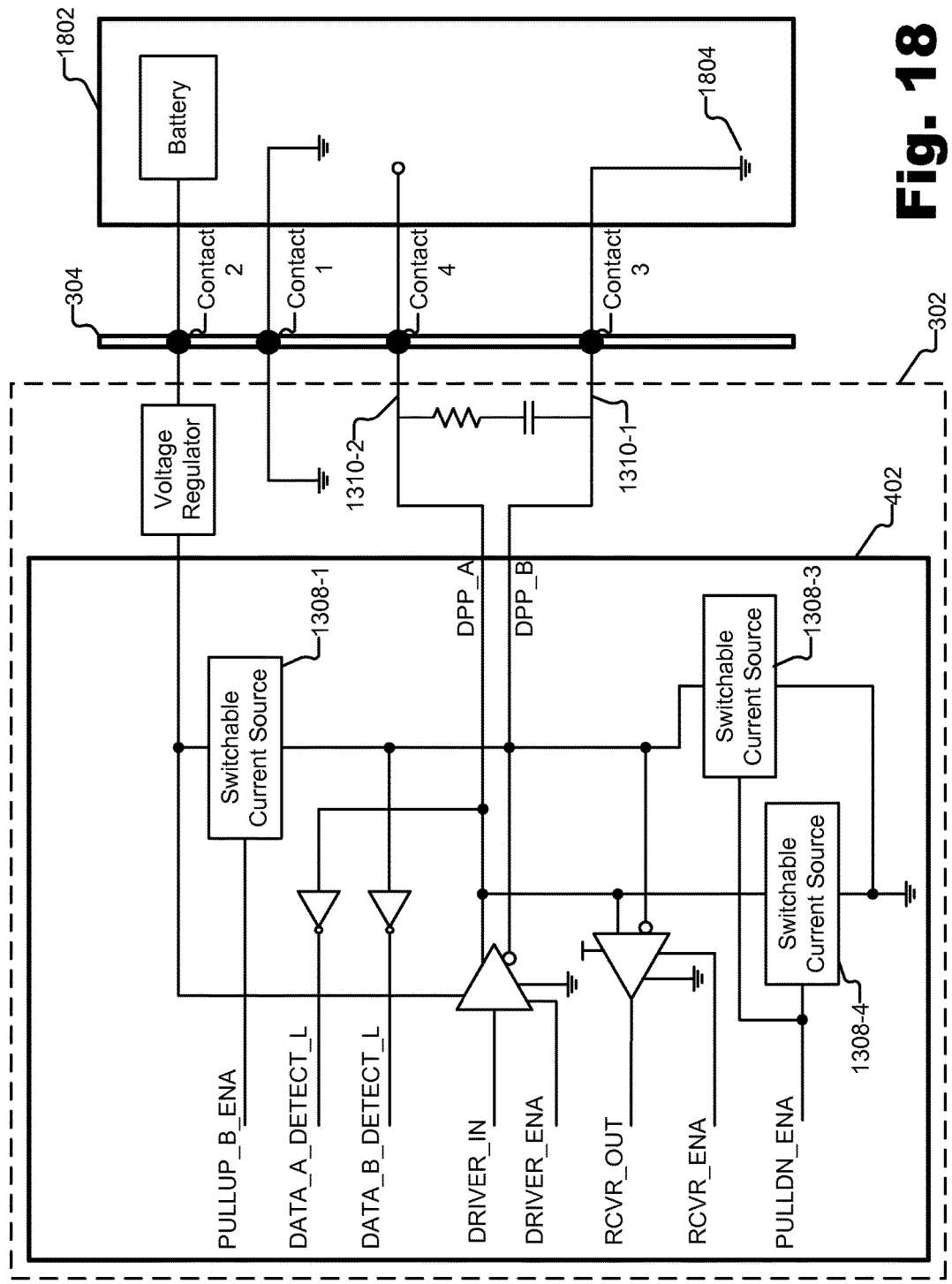

To illustrate, FIG. 18 shows an exemplary configuration wherein a single contact (i.e., contract 3) is used to identify a battery type of a battery module 1802 connected to interface facility 304. As shown, IC 402 is similar to that shown in FIGS. 13-17, except that switchable current source 1308-2 (i.e., the current source associated with data line 1310-2) is not included. Control module 304 may determine whether battery module 1802 is of a first type or a second type by determining whether contact 3 is connected to ground (i.e., ground 1804) or whether contact 3 is left open while battery module 1802 is connected to interface assembly 304. This may be performed in a similar manner to that described above in connection with FIGS. 13-17.

Control module 302 may identify the battery type (and battery model, which will be described below) of a battery module connected to interface assembly 304 at any suitable time. For example, control module 302 may identify the battery type and battery model in response to detecting a powering on of sound processor apparatus 104. Once the battery type and/or battery model is identified, control module 302 may store data representative of the identified battery type and/or model (e.g., in any suitable type of memory) and perform one or more operations in accordance with the identified battery type and/or model. For example, control module 302 may determine a remaining battery life associated with the battery module, adjust one or more control parameters associated with the auditory prosthesis system (e.g., reduce the amplitude of the electrical stimulation being applied by cochlear implant 108 in order to optimize battery usage), determine when to initiate a shut down procedure of sound processor apparatus 104 (e.g., a safe shut down procedure when battery life is almost depleted), and/or any other operation as may serve a particular implementation.

With reference again to table 1100, contacts 3 and 4 may alternatively be used by control module 302 to communicate (e.g., by using serial data communication) with a programming system (e.g., programming system 900) in accordance with a differential signaling heuristic while the programming system is connected to interface assembly 304. This function is referred to as "DPP−" and "DPP+" in table 1100.

To illustrate, control module 302 may receive programming data (e.g., programming instructions) from programming device 904 by way of pairs of differential signals transmitted via data lines associated with contacts 3 and 4 while connection interface 902 of programming system 900 is connected to interface assembly 304. In some examples, the differential signaling heuristic directs control module 302 and programming device 904 to communicate using half-duplex differential signaling (i.e., control module 302 and programming device 904 take turns driving the data lines (e.g., on a by-word or by-packet basis)).

Differential signaling provides more noise immunity than single-ended signaling, which is used in conventional communication schemes between sound processor apparatuses and programming systems. Differential signaling may also reduce EMI emissions compared to single-ended signaling.

Figure 19:
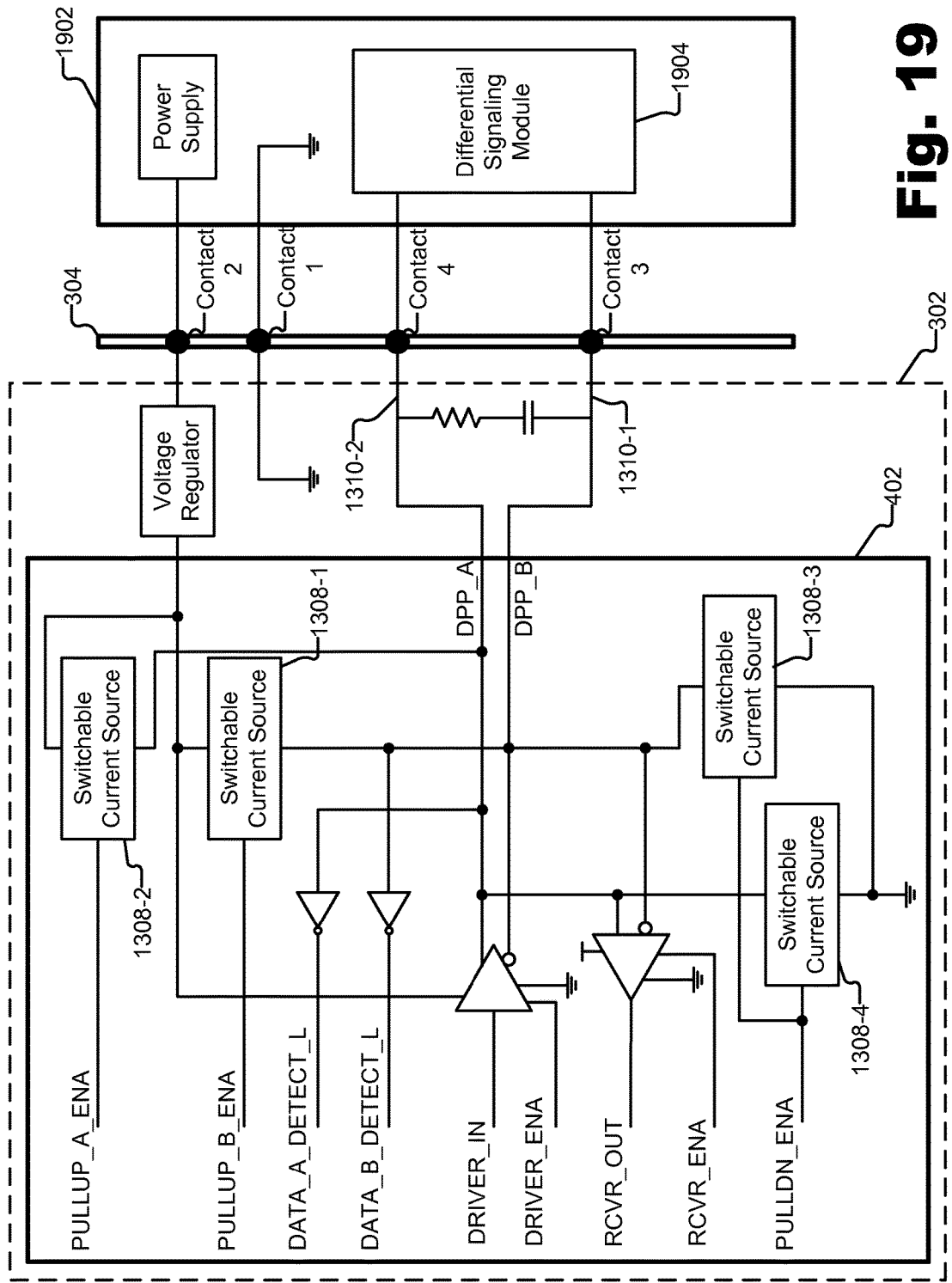

In some examples, control module 302 may detect a disconnection of a battery module (e.g., battery module 1302) from interface assembly 304 and a connection of a programming system to interface assembly 304 in place of the battery module. In response, control module 302 may switch from a battery type detection mode (i.e., a mode in which contacts 3 and 4 are used to detect a battery type) to a programming mode in which control module 302 communicates with the programming system by way of contacts 3 and 4. To illustrate, FIG. 19 shows an exemplary programming system 1902 (which may be similar to programming system 900 described above) connected to interface assembly 304 in place of a battery module (e.g., battery module 1302). As shown, contacts 3 and 4 are now connected to a differential signaling module 1904 included within programming system 1902. Differential signaling module 1904 may communicate with control module 1302 in accordance with a differential signaling heuristic.

During periods of time in which control module 302 is not actively identifying a battery type or communicating with a programming system (i.e., while control module 302 is in an idle state), control module 302 may de-assert DRIVER_ENA and assert PULLDN_ENA. This enables negative switchable current sources 1308-3 and 1308-4, which pulls data lines 1310-1 and 1310-2 to ground. This minimizes possible electrical noise due to floating inputs, and reduces corrosion risk from otherwise having these lines at non-ground potential. When in the idle state, the DATA_A_DETECT_L line can be used by control module 302 to generate an interrupt and "wake up" the control module's data communication interface, should a connected device wish to resume communication and drive data line 1310-2 high.

With reference again to table 1100, contacts 3 and 4 may alternatively be used by control module 302 as differential pulse density modulated ("PDM") audio output ports while listening check interposer 1002 is connected to interface assembly 304. This function is referred to as "PDM−" and "PDM+" in table 1100. In this manner, a user may use headphone 1004 to listen to audio that is being presented to the patient.

Various functions that may be assigned to contacts 5 and 6 will now be described. As shown in table 1100, contacts 5 and 6 may be used by control module 302 to identify a battery model associated with a particular battery module (e.g., Li-Ion battery module 602, Zn-Air battery module 604, audio enabled battery module 702, and off-ear power module 802) while the battery module is connected to interface assembly 304. This function is referred to as "MODEL ID" and "MODEL ID GND" in table 1100.

Different battery models may exist within a particular battery type. For example, two battery modules may have the same battery type, but different battery models. To illustrate, first and second battery models associated with a Li-Ion battery module may be associated with different manufacturers, have different discharge profiles, different capacities, and/or any other distinguishing characteristic as may serve a particular implementation.

Control module 302 may use contacts 5 and 6 to identify a battery model associated with a particular battery module in any suitable manner. For example, as described above, while a battery module is connected to interface assembly 304, the battery module's resistor $R_{ID}$ bridges contacts 5 and 6 of interface assembly 304. This resistor forms a loaded voltage divider in conjunction with various electrical components 404 disposed on printed circuit board 406 of sound processor apparatus 104. In some examples, each battery model has a unique resistor $R_{ID}$ value, which may result in a unique DC voltage at contact 5 (or at any other location within sound processor apparatus 104) for each battery model. Hence, the DC voltage may be detected by control module 302 and used to identify the battery model associated with a particular battery module connected to interface assembly 304.

With respect to audio-enabled battery module 702, control module 302 may use contacts 5 and 6 to identify a battery model associated with audio-enabled battery module 702 while audio-enabled battery module 702 is connected to interface assembly 304 in a similar manner as described above. For example, control module 302 may detect a DC voltage created by a resistor $R_{ID}$ that bridges contacts 5 and 6 while audio-enabled battery module 702 is connected to interface assembly 304. Resistor $R_{ID}$ may also provide the necessary load impedance to audio receiver 704.

In some examples, while audio-enabled battery module 702 is connected to interface assembly 304, a pull-up resistor internal to audio receiver 704 changes the DC bias on contact 5. This DC bias may be detected by control module 302 and used to detect a presence of audio receiver 704.

Contact 5 may also be used by control module 302 as an auxiliary audio input port while audio-enabled battery module 702 is connected to interface assembly 304. This function is referred to as "AUX" in table 1100. Contact 6 may be used by control module 302 as an audio ground associated with the auxiliary audio input port while audio-enabled battery module 702 is connected to interface assembly 304. This function is referred to as "AUX GND" in table 1100. The auxiliary audio may be provided by audio receiver 704.

Contact 5 may be concurrently used to identify a battery model and serve as an auxiliary audio input port in any suitable manner. For example, control module 302 may receive auxiliary audio input in the form of AC signals on contact 5. At the same time, control module 302 may detect a DC voltage level on contact 5 in order to identify the battery model.

With respect to programming system 900, contact 5 may be used by control module 302 as an auxiliary audio input port while programming system 900 is connected to interface assembly 304. This function is referred to as "AUX" in table 1100. Contact 6 may be used by control module 302 as an audio ground associated with the auxiliary audio input port while programming system 900 is connected to interface assembly 304. This function is referred to as "AUX GND" in table 1100. The auxiliary audio may be provided by audio receiver 706 and/or programming device 904.

Contact 5 may also be used by control module 302 (e.g., in research environments) as an evoked auditory brain stem response ("EABR") trigger output port while programming system 900 is connected to interface assembly 304. This function is referred to as "TRIG" in table 1100.

With respect to listening check interposer 1002, contacts 5 and 6 may be used by control module 302 to identify a presence of listening check interposer 1002 (i.e., that listening check interposer 1002 is connected to interface assembly 304). This function is referred to as "MODEL ID" in table 1100.

Contact 5 may also be used by control module 302 as an auxiliary audio input port while listening check interposer 1002 is connected to interface assembly 304. This function is referred to as "AUX" in table 1100. Contact 6 may be used by control module 302 as an audio ground associated with the auxiliary audio input port while listening check interposer 1002 is connected to interface assembly 304. This function is referred to as "AUX GND" in table 1100. The auxiliary audio may be provided by an audio receiver that may be connected to listening check interposer 1002.

As shown in table 1100, contact 7 may be used by control module 302 to provide power to an audio receiver attached to audio-enabled battery module 702, programming system 900, or listening check interposer 1002. This function is referred to as "AUX PWR" in table 1100. The power may be provided through a series resistor internal to control module 302 or in any other suitable manner. The supply voltage associated with the power may be of any suitable level (e.g., 1.25 V).

Contact 8 may be used by control module 302 (or by a charging device, which will be described in more detail below) to sense a temperature of battery cells included within a battery module connected to interface assembly 304. This function is referred to as "TEMP SENSE" in table 1100. Contact 8 may be used for any other function (e.g., debugging) as may serve a particular implementation.

The discussion above with respect to table 1100 has illustrated how various contacts (e.g., contacts 3 through 6) included within interface assembly 304 may be overloaded by control module 302 with different functions depending on which external component is connected to interface assembly 304. It will be recognized that any of the contacts may be overloaded with additional or alternative functions as may serve a particular implementation.

Figure 20:
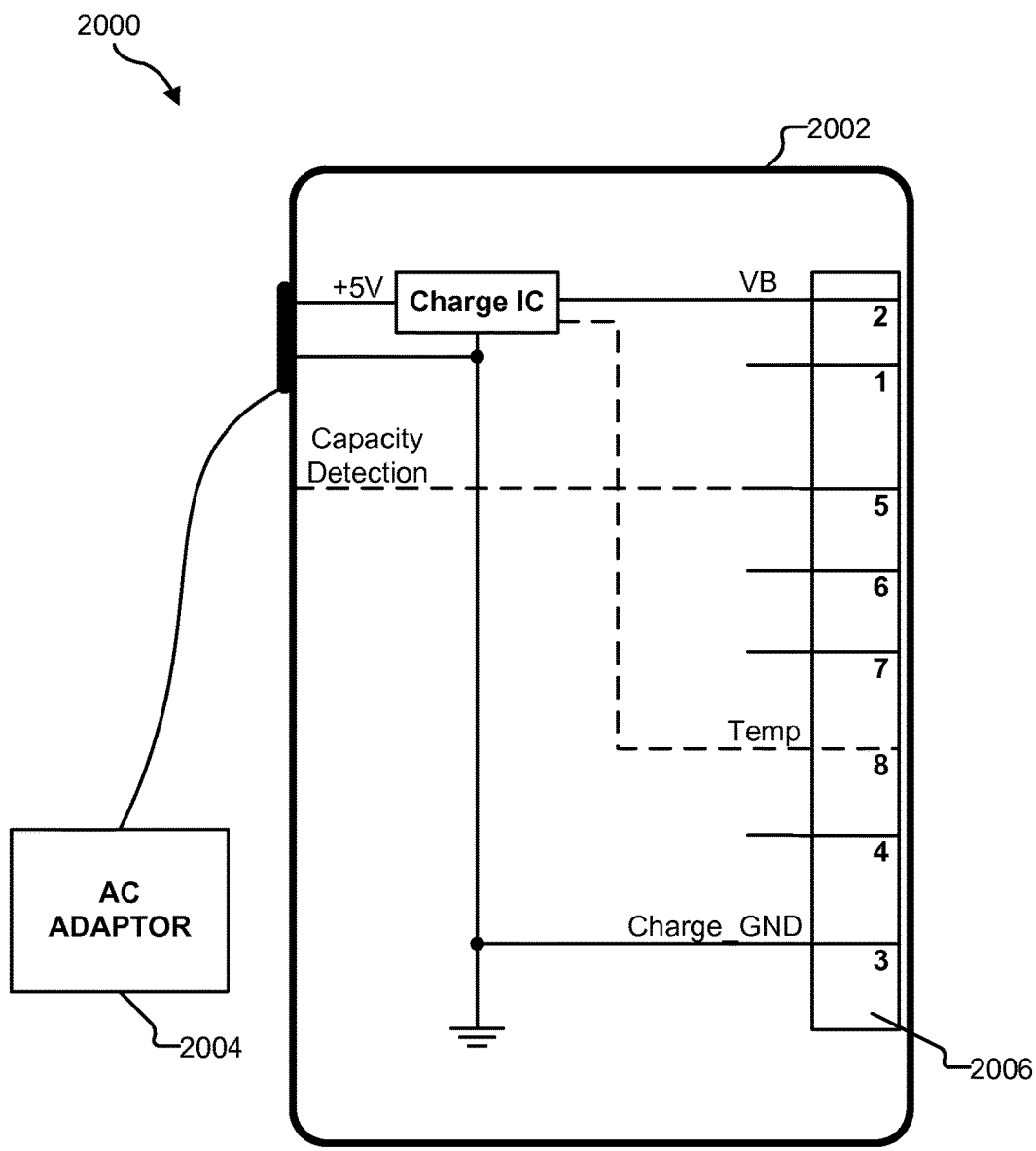
FIG. 20 illustrates an exemplary charging system according to principles described herein.

As mentioned, some types of battery modules (e.g., Li-Ion battery modules) that may be connected to interface assembly 304 are rechargeable. FIG. 20 illustrates an exemplary charging system 2000 that may be used to charge rechargeable battery modules. As shown, charging system 2000 may include a charging device 2002 communicatively coupled to an AC adaptor 2004 configured to provide operating power to charging device 2002.

As shown, charging device 2002 may include an interface assembly 2006. Interface assembly 2006 may include the same number of contacts (e.g., eight) as interface assembly 304 of sound processor apparatus 104. In this manner, battery modules configured to be connected to interface assembly 304 of sound processor apparatus 104 may be connected to interface assembly 2006 for charging by charging device 2002.

Various functions may be assigned to the contacts of interface assembly 2006. For example, contacts 2 and 3 may be used to charge a battery module that has been connected to interface assembly 2006. Contact 5 may be optionally used to detect a capacity of a battery module that has been connected to interface assembly 2006. Contact 8 may be optionally used to detect a temperature of battery cells included in a battery module that has been connected to interface assembly 2006. Temperature information acquired by contact 8 may be used by charging device 2002 to adjust a manner in which charging device 2002 charges the battery module (e.g., by adjusting a charge rate at which the battery module is charged, a charge profile, etc.).

The remaining contacts may be left open, as shown in FIG. 20. It will be recognized that additional or alternative functions may be assigned to each contact included in interface assembly 2006 as may serve a particular implementation.

In some examples, a non-rechargeable battery module may be configured to disallow charging of the non-rechargeable battery module if the non-rechargeable battery module is connected (e.g., inadvertently) to interface assembly 2006 of charging device 2002. In this manner, damage to the non-rechargeable battery module that may be caused by charging device 2002 attempting to charge the non-rechargeable battery module may be prevented.

To illustrate, as shown in FIG. 20, charging device 2002 uses contact 3 as a ground while charging a battery module connected thereto. Contact 3 of rechargeable battery modules (e.g., Li-Ion battery module 602) are connected to ground, as shown in FIG. 6, and may therefore be charged when coupled to charging device 2002. However, contact 3 of non-rechargeable battery modules (e.g., Zn-Air battery module 604) is open and therefore not connected to ground. Hence, charging of these types of battery modules cannot occur while they are coupled to charging device 2002. As a result, a non-rechargeable battery module may be connected to charging device 2002 without damaging the non-rechargeable battery module.

FIG. 21 shows a table 2100 that lists a number of use cases and how each contact included in the eight contact interface assembly 304 illustrated in FIG. 4 may be used by control module 302 in each use case. As shown, the various use cases include a normal use case (i.e., where the patient uses auditory prosthesis system 100 as he or she normally would), a normal use case with an audio-enabled battery module, a battery charging use case, a listening check use case, a device fitting use case, and a research and development ("R&D") use case. The various ways in which each contact is used during these use cases are illustrated in table 2100 and described more fully above.

Figure 22:
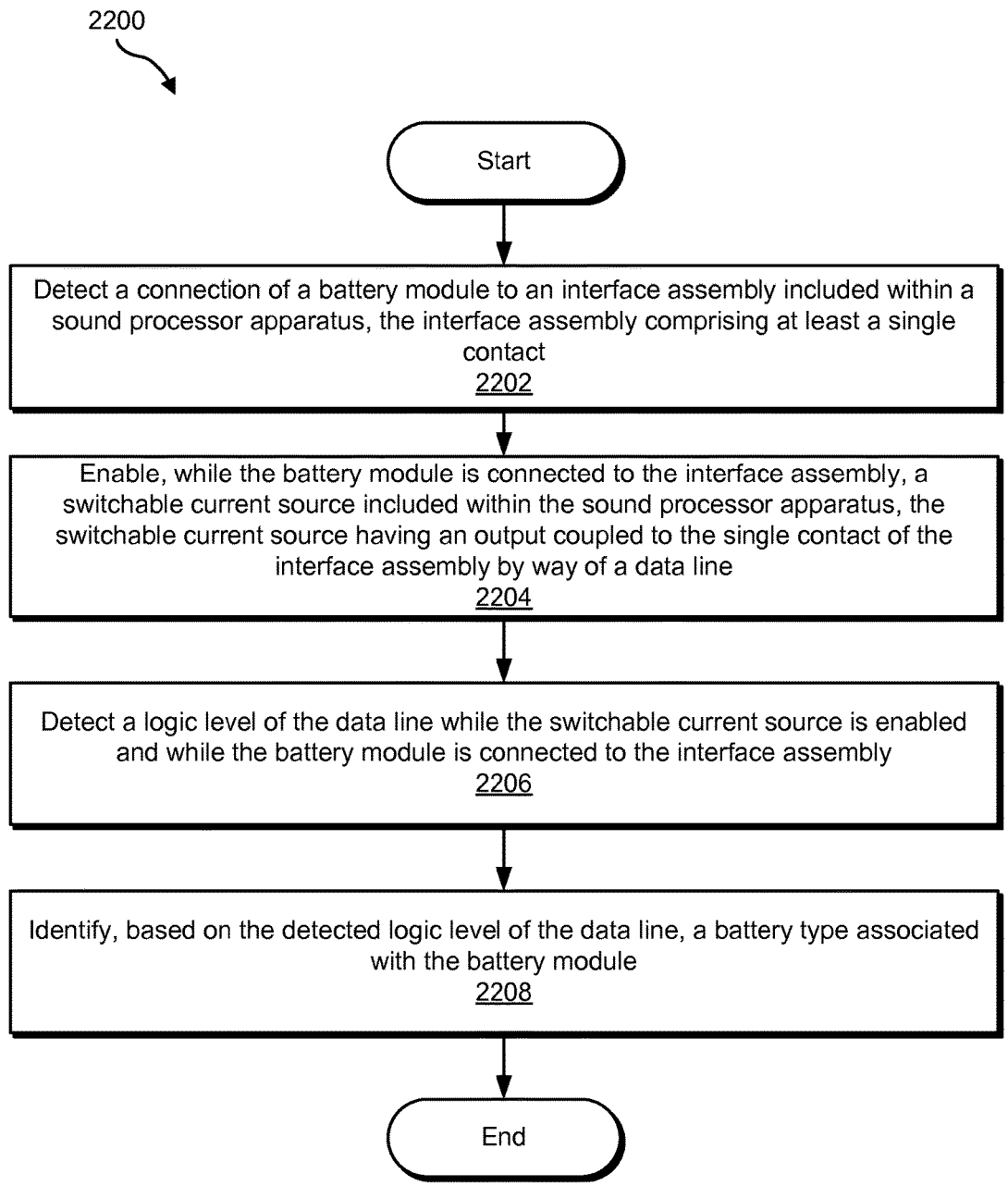
FIG. 22 illustrates an exemplary method of overloading a plurality of contacts included in an interface assembly of a sound processor apparatus that is a part of an auditory prosthesis system according to principles described herein.

FIG. 22 illustrates an exemplary method 2200 of overloading a plurality of contacts included in an interface assembly of a sound processor apparatus that is a part of an auditory prosthesis system. While FIG. 22 illustrates exemplary steps according to one embodiment, other embodiments may omit, add to, reorder, and/or modify any of the steps shown in FIG. 22. One or more of the steps shown in FIG. 22 may be performed by control module 302 and/or any implementation thereof.

In step 2202, a control module included in a sound processor apparatus that is a part of an auditory prosthesis system detects a connection of a battery module to an interface assembly included within the sound processor apparatus. The interface assembly may include at least a single contact. Step 2202 may be performed in any of the ways described herein.

In step 2204, the control module enables, while the battery module is connected to the interface assembly, a switchable current source included within the sound processor apparatus, the switchable current source having an output coupled to the single contact of the interface assembly by way of a data line. Step 2204 may be performed in any of the ways described herein.

In step 2206, the control module detects a logic level of the data line while the switchable current source is enabled and while the battery module is connected to the interface assembly. Step 2206 may be performed in any of the ways described herein.

In step 2208, the control module identifies, based on the detected logic level of the data line, a battery type associated with the battery module. Step 2208 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A sound processor apparatus included in an auditory prosthesis system and comprising:
   an interface assembly that includes at least a first contact and a second contact and that facilitates interchangeable connectivity of a plurality of external components to the sound processor apparatus, the plurality of external components comprising a battery module and a programming system that is configured to fit the auditory prosthesis system to a patient;
   a first switchable current source having an output coupled to the first contact of the interface assembly by way of a first data line; and
   a control module communicatively coupled to the first and second contacts, to the first switchable current source, and to the first data line and configured to selectively operate in a battery type detection mode and in a programming mode,
   wherein, while operating in the battery type detection mode, the control module:
   enables the first switchable current source while the battery module is connected to the interface assembly by way of the first and second contacts,
   detects a logic level of the first data line while the first switchable current source is enabled and while the battery module is connected to the interface assembly, and
   identifies, based on the detected logic level of the first data line and using the first and second contacts, a battery type of the battery module, and
   wherein, while operating in the programming mode, the control module:
   detects a connection of the programming system to the interface assembly by way of the first and second contacts in place of the battery module, and
   uses a differential signaling heuristic to communicate with the programming system by way of the first and second contacts while the programming system is connected to the interface assembly by way of the first and second contacts.

2. The sound processor apparatus of claim 1, wherein the control module:
   detects a logic low as the logic level of the first data line if the connection of the battery module to the interface assembly causes the first contact to become connected to a ground located within the battery module; and
   detects a logic high as the logic level of the first data line if the connection of the battery module to the interface assembly causes the first contact to remain open without being connected to the ground located within the battery module.

3. The sound processor apparatus of claim 2, wherein the control module:
   identifies the battery type as being a first battery type if the logic low is detected; and
   identifies the battery type as being a second battery type if the logic high is detected.

4. The sound processor apparatus of claim 3, wherein the first battery type is associated with a first voltage range and the second battery type is associated with a second voltage range different than the first voltage range.

5. The sound processor apparatus of claim 1, wherein the control module:
   detects a logic low as the logic level of the first data line if the battery module comprises a pull-down resistor coupled to a data line located within the battery module and that connects to the first contact when the battery module connects to the interface assembly; and
   detects a logic high as the logic level of the first data line if the battery module does not comprise the pull-down resistor.

6. The sound processor apparatus of claim 1, wherein:
the sound processor apparatus further comprises a second switchable current source having an output coupled to the second contact of the interface assembly by way of a second data line; and
the control module is further communicatively coupled to the second switchable current source and to the second data line and further
enables the second switchable current source while the battery module is connected to the interface assembly, and
detects a logic level of the second data line while the second switchable current source is enabled and while the battery module is connected to the interface assembly;
wherein the identification by the control module of the battery type is further based on the detected logic level of the second data line.

7. The sound processor apparatus of claim 6, wherein the control module identifies the battery type by:
identifying the battery type as a first battery type if the detected logic level of the first data line and the detected logic level of the second data line are both logic lows;
identifying the battery type as a second battery type if the detected logic level of the first data line is a logic low and the detected logic level of the second data line is a logic high;
identifying the battery type as a third battery type if the detected logic level of the first data line is a logic high and the detected logic level of the second data line is a logic low; and
identifying the battery type as a fourth battery type if the detected logic level of the first data line and the detected logic level of the second data line are both logic highs.

8. The sound processor apparatus of claim 6, wherein the control module disables the first switchable current source in response to the identifying of the battery type associated with the battery module.

9. The sound processor apparatus of claim 8, further comprising:
a third switchable current source having an output coupled to the first data line;
wherein the control module is further communicatively coupled to the third switchable current source and configured to enable the third switchable current source in response to the disabling of the first switchable current source; and
wherein the enabling of the third switchable current source causes the third switchable current source to pull the first data line to a ground state.

10. The sound processor apparatus of claim 1, wherein the control module uses differential signaling to communicate with the programming system by receiving programming instructions from the programming system by way of the first and second contacts in the form of one or more differential signals.

11. The sound processor apparatus of claim 1, wherein the control module:
detects a powering on of the sound processor apparatus; and
enables the first switchable current source in response to the powering on of the sound processor apparatus.

12. The sound processor apparatus of claim 1, wherein the control module further performs one or more operations in accordance with the identified battery type.

13. The sound processor apparatus of claim 12, wherein the one or more operations include at least one of determining a remaining battery life associated with the battery module, adjusting one or more control parameters associated with the auditory prosthesis system, and determining when to initiate a shut down procedure of the sound processor apparatus.

14. The sound processor apparatus of claim 1, wherein:
the interface assembly further includes a third contact; and
the control module uses the second and third contacts to identify a battery model associated with the battery module.

15. The sound processor apparatus of claim 14, wherein the control module uses the second and third contacts to identify the battery model associated with the battery module by:
detecting a voltage level at the second contact that depends on a value of a resistor included within the battery module and that bridges the second and third contacts while the battery module is connected to the interface assembly; and
using the detected voltage level to identify the battery model.

16. The sound processor apparatus of claim 1, further comprising a casing that houses the interface assembly, the first switchable current source, and the control module.

17. A sound processor apparatus included in an auditory prosthesis system and comprising:
an interface assembly that includes at least a first contact and a second contact and that facilitates interchangeable connectivity of a plurality of external components to the sound processor apparatus, the plurality of external components comprising a battery module and a programming system that is configured to fit the auditory prosthesis system to a patient; and
a control module coupled to the first and second contacts and configured to selectively operate in a battery type detection mode and in a programming mode;
wherein, while operating in the battery type detection mode, the control module uses the first and second contacts to detect a battery type of the battery module while the battery module is connected to the interface assembly;
wherein, while operating in the programming mode, the control module uses the first and second contacts to communicate with the programming system while the programming system is connected to the interface assembly; and
wherein the control module uses the first and second contacts to communicate with the programming system by using the first and second contacts to communicate with the programming system in accordance with a differential signaling heuristic.

18. A method comprising:
detecting, by a control module included within a sound processor apparatus that is a part of an auditory prosthesis system, a connection of a battery module to an interface assembly included within the sound processor apparatus, the interface assembly comprising at least a first contact and a second contact and facilitating interchangeable connectivity of a plurality of external components to the sound processor apparatus, the plurality of external components comprising the battery module and a programming system that is configured to fit the auditory prosthesis system to a patient, and the control module coupled to the first and second contacts and configured to selectively operate in a battery type detection mode and in a programming mode;

wherein, while operating in the battery type detection mode:

enabling, by the control module while the battery module is connected to the interface assembly, a switchable current source included within the sound processor apparatus, the switchable current source having an output coupled to the first contact of the interface assembly by way of a data line;

detecting, by the control module, a logic level of the data line while the switchable current source is enabled and while the battery module is connected to the interface assembly; and identifying, by the control module based on the detected logic level of the data line and using the first and second contacts, a battery type of the battery module; and wherein, while operating in the programming mode:

detecting, by the control module, a connection of the programming system to the interface assembly by way of the first and second contacts in place of the battery module; and using, by the control module subsequent to the detecting of the connection of the programming system, a differential signaling heuristic to communicate with the programming system by way of the first and second contacts while the programming system is connected to the interface assembly by way of the first and second contacts.

* * * * *